(12) United States Patent
Chappa

(10) Patent No.: US 8,668,667 B2
(45) Date of Patent: Mar. 11, 2014

(54) DOUBLE WALL CATHETER FOR DELIVERING THERAPEUTIC AGENT

(75) Inventor: Ralph A. Chappa, Ham Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 79 days.

(21) Appl. No.: 13/339,926

(22) Filed: Dec. 29, 2011

(65) Prior Publication Data

US 2012/0172839 A1 Jul. 5, 2012

Related U.S. Application Data

(60) Provisional application No. 61/428,353, filed on Dec. 30, 2010.

(51) Int. Cl.
*A61M 29/00* (2006.01)

(52) U.S. Cl.
USPC .................................. 604/101.02; 604/103.02

(58) Field of Classification Search
USPC .................. 604/101.01, 101.02, 102.01, 509
See application file for complete search history.

(56) References Cited

U.S. PATENT DOCUMENTS

| | | | |
|---|---|---|---|
| 4,195,637 A | 4/1980 | Grüntzig et al. | |
| 4,490,421 A | 12/1984 | Levy | |
| 4,994,033 A * | 2/1991 | Shockey et al. | 604/101.02 |
| 5,002,582 A | 3/1991 | Guire et al. | |
| 5,041,089 A | 8/1991 | Mueller et al. | |
| 5,087,246 A | 2/1992 | Smith | |
| 5,318,587 A | 6/1994 | Davey | |
| 5,382,234 A | 1/1995 | Cornelius et al. | |
| 5,414,075 A | 5/1995 | Swan et al. | |
| 5,556,383 A | 9/1996 | Wang et al. | |
| 5,571,089 A | 11/1996 | Crocker | |
| 5,714,360 A | 2/1998 | Swan et al. | |
| 5,776,101 A | 7/1998 | Goy | |
| 5,807,331 A | 9/1998 | den Heijer et al. | |
| 5,882,336 A | 3/1999 | Janacek | |
| 6,007,833 A | 12/1999 | Chudzik et al. | |
| 6,168,748 B1 | 1/2001 | Wang et al. | |
| 6,210,364 B1 | 4/2001 | Anderson et al. | |
| 6,328,710 B1 | 12/2001 | Wang et al. | |
| 6,394,995 B1 | 5/2002 | Solar et al. | |
| 6,482,348 B1 | 11/2002 | Wang et al. | |
| 6,485,500 B1 * | 11/2002 | Kokish et al. | 606/194 |
| 6,517,515 B1 | 2/2003 | Eidenschink | |
| 6,544,579 B1 | 4/2003 | Landon | |
| 6,610,317 B2 | 8/2003 | Straub et al. | |

(Continued)

FOREIGN PATENT DOCUMENTS

WO   WO 2009/036118 A1   3/2009

OTHER PUBLICATIONS

PCT International Preliminary Report on Patentability, International Application No. PCT/US2011/067722, mailed Jul. 11, 2013.

*Primary Examiner* — Aarti B Berdichevsky
(74) *Attorney, Agent, or Firm* — Kagan Binder, PLLC

(57) ABSTRACT

The present invention relates to a catheter assembly that can deliver a therapeutic composition. The catheter assembly can include an outer balloon with openings for releasing the therapeutic composition. When the catheter assembly is in its contracted state, the openings are closed, and the assembly retains the therapeutic composition. When the catheter assembly is in its dilated state, the openings are open, and the therapeutic composition is released. The present invention also includes methods of making and using such a catheter assembly.

21 Claims, 8 Drawing Sheets

(56) References Cited

U.S. PATENT DOCUMENTS

| | | |
|---|---|---|
| 6,623,504 B2 | 9/2003 | Vrba et al. |
| 6,896,842 B1 | 5/2005 | Hamilton et al. |
| 7,163,523 B2 | 1/2007 | Devens, Jr. et al. |
| 7,935,044 B2 * | 5/2011 | Lubock ............................ 600/3 |
| 2006/0079836 A1 | 4/2006 | Holman et al. |
| 2006/0190022 A1 | 8/2006 | Beyar et al. |
| 2009/0028956 A1 | 1/2009 | Slager et al. |
| 2010/0125239 A1 * | 5/2010 | Perry et al. ...................... 604/21 |
| 2010/0266656 A1 | 10/2010 | Johnson |
| 2011/0060275 A1 * | 3/2011 | Christiansen ............ 604/101.02 |
| 2011/0144373 A1 | 6/2011 | Swan et al. |
| 2011/0245367 A1 | 10/2011 | Kurdyumov et al. |
| 2012/0165786 A1 * | 6/2012 | Chappa et al. ................ 604/509 |
| 2012/0172796 A1 * | 7/2012 | Chappa ................... 604/101.02 |

* cited by examiner

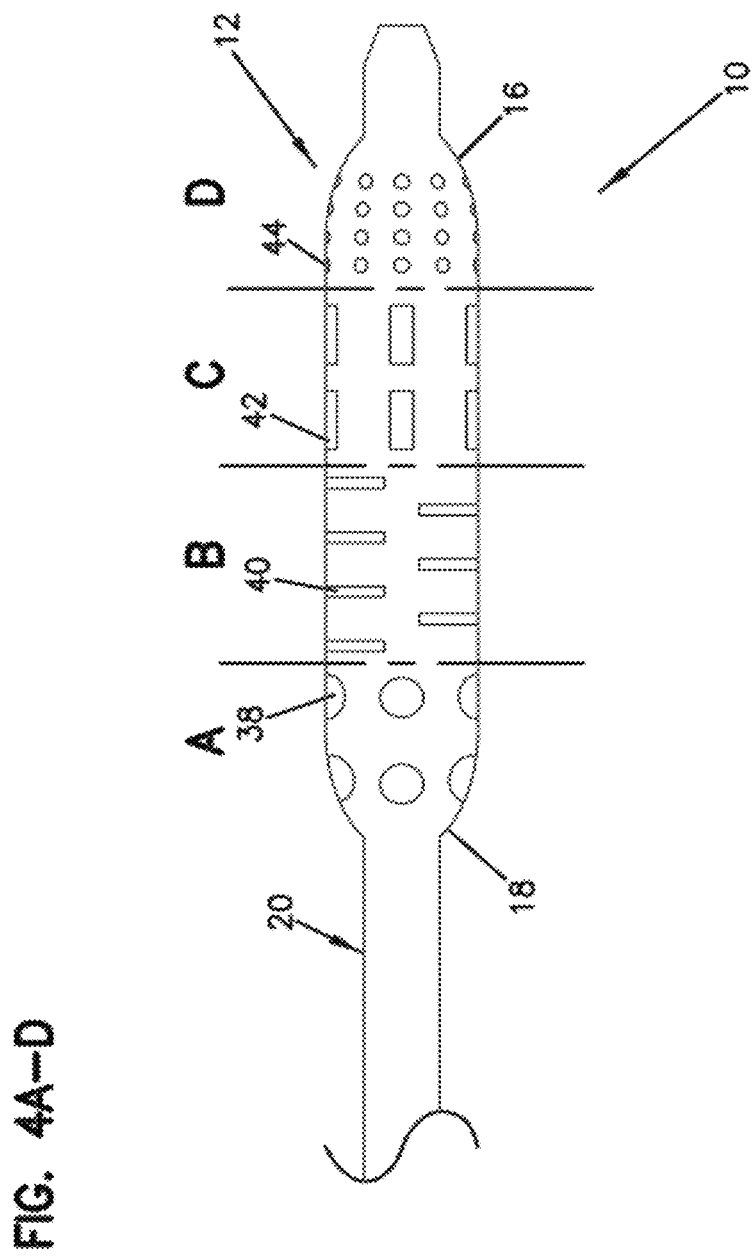
FIG. 4A-D

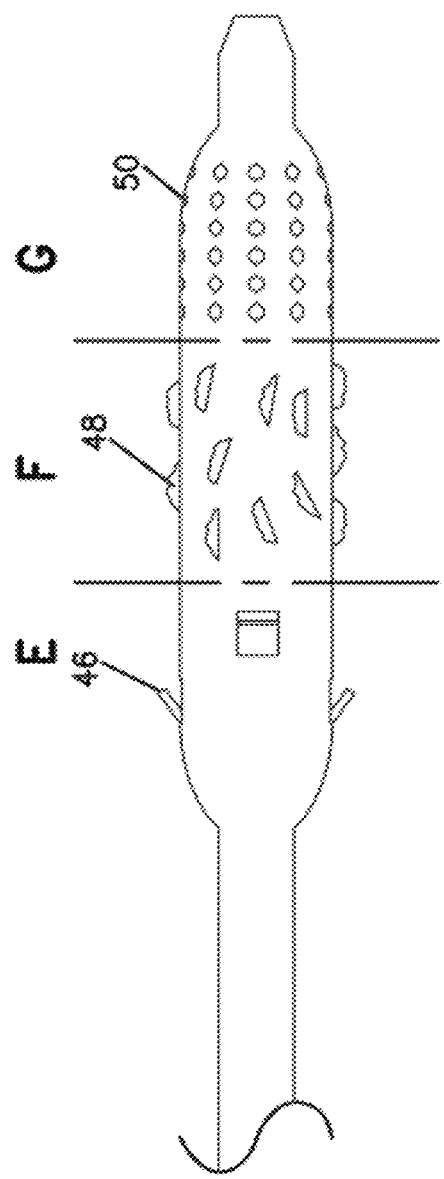
FIG. 4E–G

DOUBLE WALL CATHETER FOR DELIVERING THERAPEUTIC AGENT

CROSS-REFERENCE TO RELATED APPLICATION

This application claims benefit of U.S. Provisional Application No. 61/428,353, filed Dec. 30, 2010, which application is incorporated herein by reference.

FIELD OF THE INVENTION

The present invention relates to a catheter assembly that can deliver a therapeutic composition. An embodiment of the present catheter assembly can protect a liquid therapeutic composition from its surroundings by retaining it in a reservoir between an inner and outer balloon. The therapeutic composition can be released from the assembly through openings in the outer balloon. When the assembly is in its contracted state, the openings are closed, and the assembly retains the therapeutic composition. Expanding the inner balloon (e.g., with fluid) urges the assembly to its dilated state, in which the openings are open, and the therapeutic composition can leave the assembly. A lumen in fluid communication with the reservoir can increase the capacity of the assembly for the therapeutic composition. The present invention also includes methods of making and using such a catheter assembly.

BACKGROUND OF THE INVENTION

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body.

Some implantable devices simply have a drug applied to the device surface. Such preparations are generally undesirable because the drug can be easily removed from the surface during insertion.

Implantable medical devices having thin polymeric coatings containing therapeutic compounds protect and control the release of drug from the device surface. Such devices have been shown to be particularly valuable for the treatment of diseases of the cardiovascular system. However, these polymeric coatings may not be ideal for applications involving the transient insertion of a medical device to a target tissue in the body.

SUMMARY OF THE INVENTION

The present invention relates to a catheter assembly that can deliver a therapeutic composition. An embodiment of the present catheter assembly can protect a liquid therapeutic composition from its surroundings by retaining it in a reservoir between an inner and outer balloon. The therapeutic composition can be released from the assembly through openings in the outer balloon. When the assembly is in its contracted state, the openings are closed, and the assembly retains the therapeutic composition. Expanding the inner balloon (e.g., with fluid) urges the assembly to its dilated state, in which the openings are open, and the therapeutic composition can leave the assembly. A lumen in fluid communication with the reservoir can increase the capacity of the assembly for the therapeutic composition. The present invention also includes methods of making and using such a catheter assembly.

In an embodiment, the present catheter assembly includes an inner expandable and collapsible structure and an outer expandable and collapsible structure. The inner and outer expandable and collapsible structures can be configured to expand between a contracted state and a dilated state. The inner and outer expandable and collapsible structures define a cavity therebetween, which is configured to contain a benefit composition. The outer expandable and collapsible structure defines openings. The openings being configured to be closed when the assembly is in the contracted state. The openings are configured to be open when the assembly is in the dilated state. When open, the openings provide fluid communication from the cavity to surroundings of the assembly.

In another aspect, the present invention includes a method of delivering a bioactive agent to a site in a body. The method employs the present catheter assembly. This method includes placing the catheter assembly at the site and actuating the catheter assembly from the contracted state to the dilated state to release the bioactive agent.

BRIEF DESCRIPTION OF THE FIGURES

FIGS. 4A through 4G are schematic representations of configurations of openings in the external expandable and collapsible structure.

FIG. 5A shows the structure in its contracted state. FIG. 5B shows the structure in its dilated state.

FIG. 6A shows the structure in its contracted state. FIG. 6B shows the structure in its dilated state.

FIG. 7A shows the structure in its contracted state. FIG. 7B shows the structure in its dilated state.

DETAILED DESCRIPTION OF THE INVENTION

Figure 1:
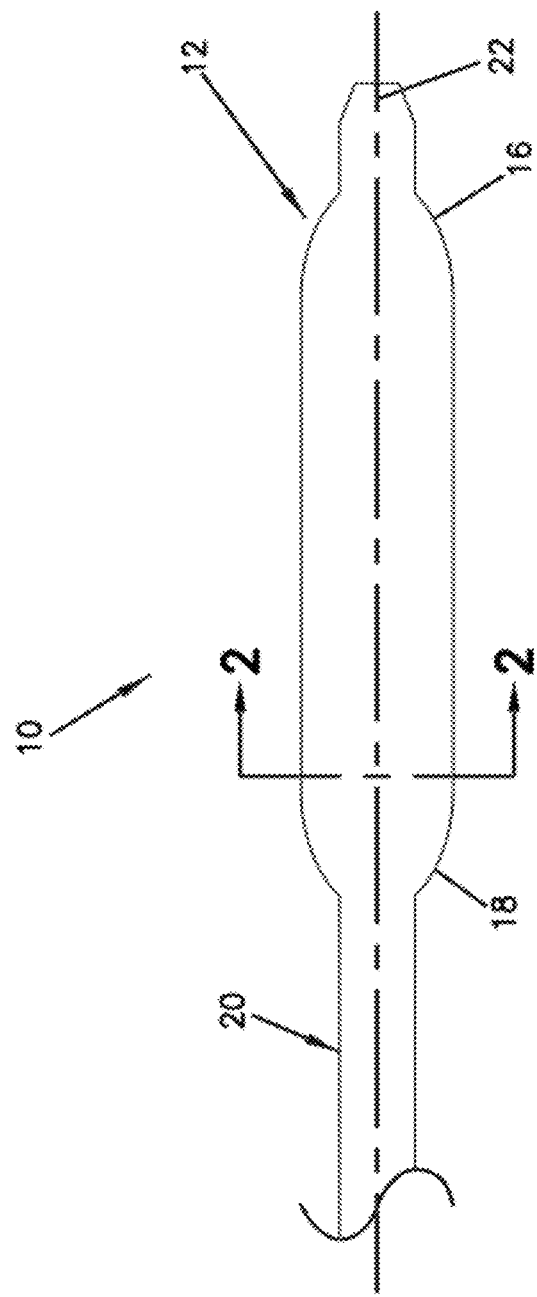
FIG. 1 is a schematic representation of a side view of an embodiment of the present catheter assembly.

The present invention relates to a catheter for delivering a therapeutic agent. The catheter can be a balloon catheter with two balloons, one inside the other. The therapeutic composition can be in a reservoir between the two balloons. Such a catheter can retain a liquid (e.g., water miscible) therapeutic composition. Such a catheter can protect a therapeutic composition that might react with surroundings of the catheter in a subject. The volume of therapeutic composition within the catheter can be increased by including a lumen (e.g., a "third" lumen) in fluid communication with the reservoir.

A coating or therapeutic composition on the exterior of an insertable medical device can be degraded or removed before the device is at the location within a subject at which the therapeutic composition is intended to be released or to act. In an embodiment, the present catheter protects a therapeutic composition from the surroundings (e.g., the environment outside the subject and the subject's tissues and bodily fluids) until the composition is at the location at which it is intended to be released from the catheter. The therapeutic composition is in the reservoir between the two balloons, and the two balloons can protect the therapeutic composition from contact or reaction with the surroundings. Any therapeutic composition in the lumen that is in fluid communication with the reservoir can also be protected.

A water miscible liquid coating or therapeutic composition on the exterior of an insertable medical device is unlikely to remain on the device as it moves through the subject to the location at which the therapeutic composition is intended to be released or to act. In an embodiment, the present catheter retains a water miscible liquid coating or therapeutic composition within the catheter (e.g., the reservoir and/or the "third" lumen) until the liquid is at the location at which it is intended to be released from the catheter.

The volume of a coating or therapeutic agent on the exterior of an insertable medical device is limited by the occupied surface area and the thickness of the coating. In an embodiment, the present catheter provides an advantageously large volume of therapeutic composition for delivery to the desired release site. The advantageously large volume can be made up of the reservoir and/or the "third" lumen that is in fluid communication with and that can contain the therapeutic composition.

The present device can include and deliver any of a variety of therapeutic compositions. The therapeutic composition is in a form that can exit or be expelled from the device through the apertures in the outer balloon. In certain embodiments, the therapeutic composition can be in the form of a liquid (e.g., saline solution of bioactive agent), lipid composition, gel, paste, oil, grease, or other flowable composition that is suitable for administration to a mammal (e.g., a human). In an embodiment, the therapeutic composition is liquid, such as a water miscible liquid. The therapeutic composition includes a bioactive agent. In certain embodiments, the therapeutic composition can be a flowable composition that is or includes a biocompatible grease, oil, or other matrix combined with a bioactive agent.

In an embodiment, the therapeutic composition includes an active agent that can react with or precipitate in the surroundings of the device in a subject. The catheter assembly protects such an active agent from the surroundings. In an embodiment, the therapeutic composition, when released from the present catheter assembly, reacts or hardens to form a structure outside the catheter assembly. The structure formed from the therapeutic composition can be, for example, a stent.

The first or inner balloon can be expanded by introducing fluid (e.g., saline) into a lumen. The second or outer balloon includes apertures that are closed when this balloon is in a first or closed position. The apertures can be open when the second balloon is in its second or open position. Expansion of the inner balloon urges the outer balloon from its closed position to its open position, e.g., applies outward pressure to the outer balloon. Expansion of the inner balloon can also urge the therapeutic composition through the apertures.

The apertures of the outer balloon can be closed by any of a variety of mechanisms. For example, the apertures can be sealed by a material (e.g., a coating or layer) on the external surface of the outer balloon. For example, the apertures can be sealed by coupling or cross linking one or more of the edges that define the aperture. For example, the outer balloon can be made of a material that is sufficiently rigid that the apertures remain closed in the absence of force applied to expand or stretch the outer balloon. For example, the outer balloon can be made of a material that becomes permeable to the therapeutic composition (e.g., porous) as force is applied to expand or stretch the outer balloon.

The present invention relates to a catheter assembly that can deliver a therapeutic composition. The catheter assembly can include an outer balloon with openings for releasing the therapeutic composition. When the catheter assembly is in its contracted state, the openings are closed, and the assembly retains the therapeutic composition. When the catheter assembly is in its dilated state, the openings are open, and the therapeutic composition is released. The therapeutic composition can be water miscible or can contain an active agent that could react with the surroundings. The catheter assembly can protect such a composition. The present invention also includes methods of making and using such a catheter assembly.

Illustrated Embodiments

Reference will now be made in detail to certain aspects of the present disclosure that are illustrated in the accompanying drawings. Wherever possible, the same reference numbers will be used throughout the drawings to refer to the same or like structure.

Referring now to FIG. 1, a catheter assembly 10 is shown. The catheter assembly 10 is adapted to provide a drug delivery system that retains a therapeutic composition as the catheter assembly 10 is guided to a target site to release the composition.

In the depicted embodiment, the catheter assembly 10 is adapted for use in medical procedures such as angioplasty. In an angioplasty procedure, the catheter assembly 10 is inserted into a blood vessel of a patient and guided to a target site in the vasculature of the patient. In one example, the target site is a location at which there is a blockage in a blood vessel that is restricting flow through that blood vessel.

In the subject embodiment, the catheter assembly 10 includes agent delivery structure 12. The agent delivery structure 12 of the catheter assembly 10 is expanded from a contracted state (shown in FIGS. 1 and 2) to a dilated state (shown in FIG. 3) at the target site and subsequently collapsed from the dilated state to the contracted state. In an example, dilation of the agent delivery structure 12 compresses artheroma at the target site in the blood vessel. A benefit composition 14 within the agent delivery structure 12 is delivered to the tissue at or surrounding the target site when the agent delivery structure 12 is in the dilated state. The benefit composition 14 is an embodiment of the therapeutic composition. Referring now to the figures of the present disclosure, the catheter assembly 10 and the use of the catheter assembly 10 will be further described.

Figure 2:
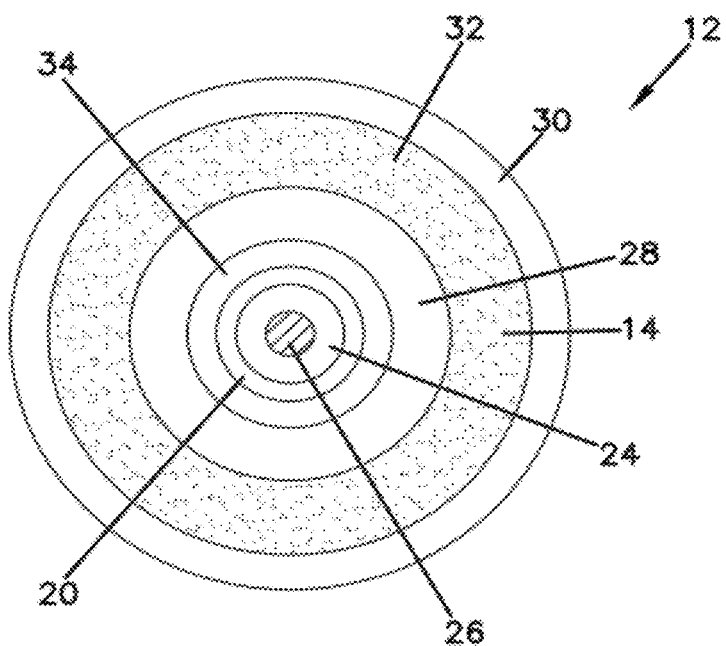
FIG. 2 is a cross-sectional view of the catheter assembly taken on line 2-2 of FIG. 1 with the catheter in the contracted state.
Figure 3:
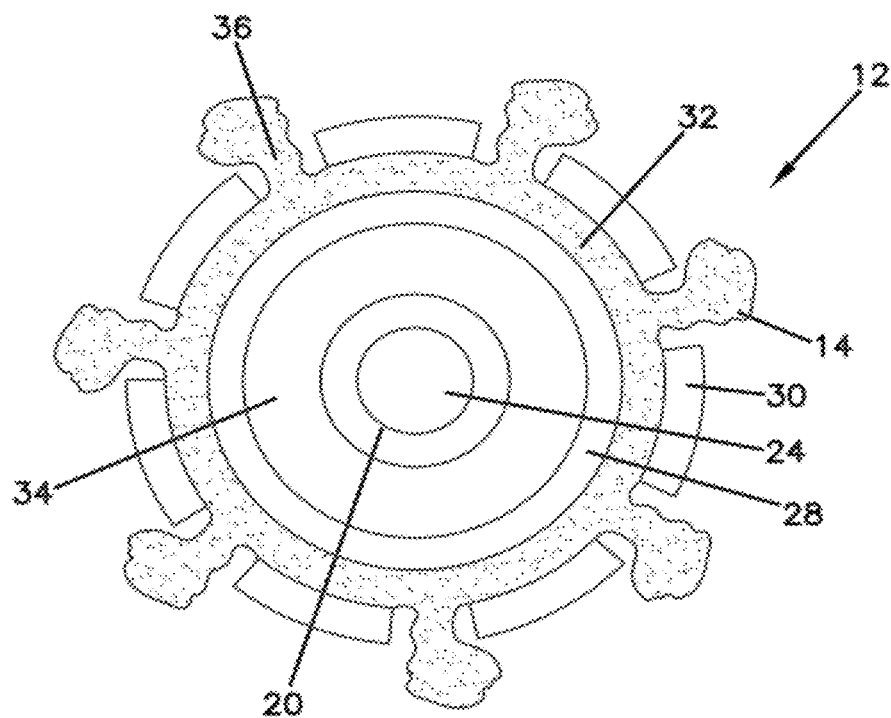
FIG. 3 is a cross-sectional view of the catheter assembly taken on line 2-2 of FIG. 1 with the catheter in the dilated state.

Referring now to FIG. 1-3, the agent delivery structure 12 includes a distal end 16 and a proximal end 18 and a shaft 20 that defines a central longitudinal axis 22 that extends through the distal and proximal ends 16, 18. The agent delivery structure 12 also includes a guide passage 24 that extends through the distal and proximal ends 16 and 18. The guide passage 24 is adapted to receive a guide wire 26 along which the catheter assembly 10 passes to the target site in the blood vessel of a body of the patient.

The agent delivery structure 12 includes a first or inner expandable and collapsible structure 28 and a second or external expandable and collapsible structure 30. First or inner expandable and collapsible structure 28 is an embodiment of the first or inner balloon. Second or outer external expandable and collapsible structure 30 is an embodiment of the second or outer balloon. The first and second expandable and collapsible structures 28 and 30 define a cavity 32 that contains the benefit composition 14. The cavity 32 is an embodiment of the reservoir.

The agent delivery structure 12 defines a lumen 34 disposed between the inner expandable and collapsible structure 28 and the shaft 20. The lumen 34 is configured to receive a fluid (e.g., saline) to expand the agent delivery structure 12 to the dilated state. When fluid is communicated to the lumen 32, the fluid exerts a radially outward force on the inner and outer expandable and collapsible structures 28 and 30. This radially outward force causes the agent delivery structure 12 to dilate to the dilated state (FIG. 3). When the fluid in the lumen 34 is drained, the agent delivery structure 12 collapses or shrinks to the contracted state.

In the dilated state, opening(s) 36 has opened in outer expandable and collapsible structure 30 (FIG. 3). The opening 36 is an embodiment of the aperture. Through the openings 36, benefit composition 14 can escape the agent delivery structure 12 and contact a subject's nearby tissue. Outer expandable and collapsible structure 30 and opening 36 can be in any of a variety of configurations. For example, opening 36 can have the shape of a circle 38 (FIG. 4A), circumferentially oriented slot 40 (FIG. 4B), axially oriented slot 42 (FIG. 4C), perforation 44 (FIG. 4D), flapped opening 46 (FIG. 4E), pore 48 (shown with therapeutic composition coming through them) (FIG. 4F), or ovoid 50 (FIG. 4G).

Figure 5A:
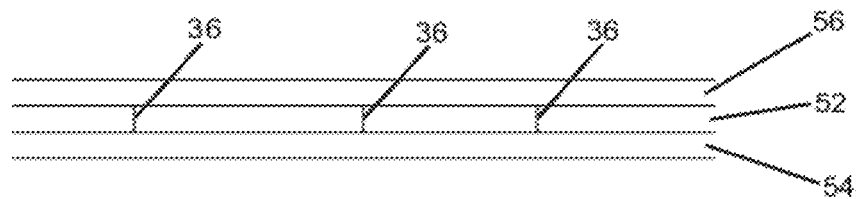
FIGS. 5A and 5B schematically represent an embodiment of the external expandable and collapsible structure including an inner and outer scissile coating.
Figure 6A:
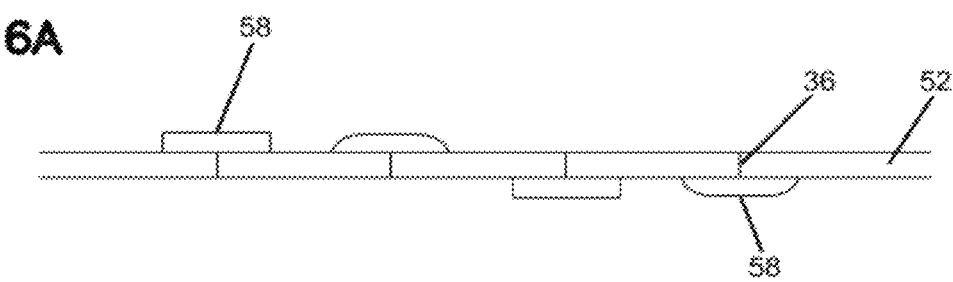
FIGS. 6A and 6B schematically represent an embodiment of the external expandable and collapsible structure including scissile patches.

In the contracted state, the opening(s) 36 in the outer expandable and collapsible structure 30 are closed, sealed, or are absent (e.g., unformed pores) (FIG. 2). The outer expandable and collapsible structure 30 can be include any of a variety of features that maintain the openings in their closed configuration. For example, the outer expandable and collapsible structure 30 can include expandable and contractible membrane 52 and one or both of inner scissile coating 54 and outer scissile coating 56 (FIG. 5A). The inner and/or outer scissile coatings 54 and 56 can be continuous or discontinuous on the expandable and contractible membrane 52, but cover the locations of the closed openings 36. For example, the inner and/or outer scissile coatings 54 and 56 can be in the form of scissile patch 58 (FIG. 6A).

Figure 5B:
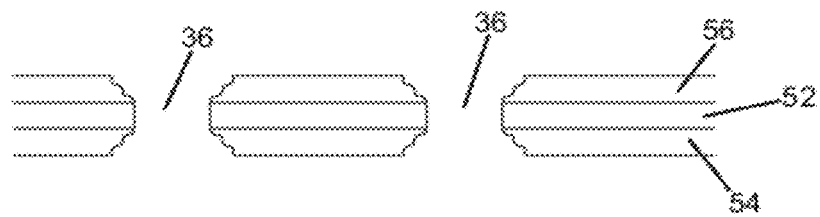
Figure 6B:
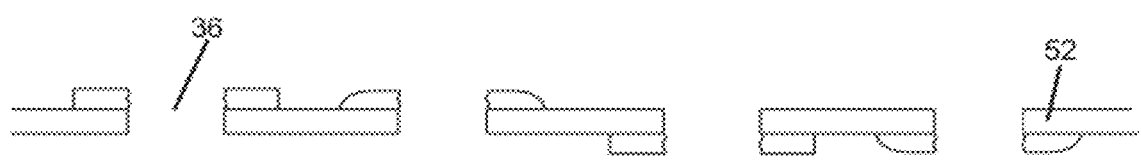

In the dilated state, the opening(s) 36 has opened through expandable and contractible membrane 52 and the inner scissile coating 54 and/or outer scissile coating 56, depending upon whether one or both are present, (FIG. 5B). In an embodiment, opening(s) 36 has opened through expandable and contractible membrane 52 and the scissile patch 58 (FIG. 6B).

Figure 7A:
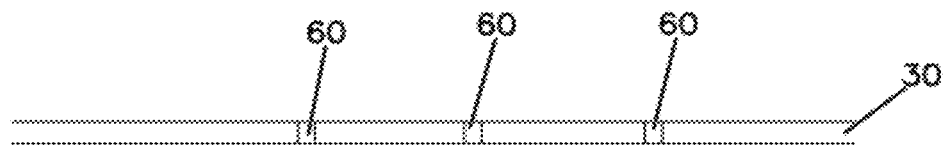
FIGS. 7A and 7B schematically represent an embodiment of the external expandable and collapsible structure including scissile plugs.
Figure 7B:
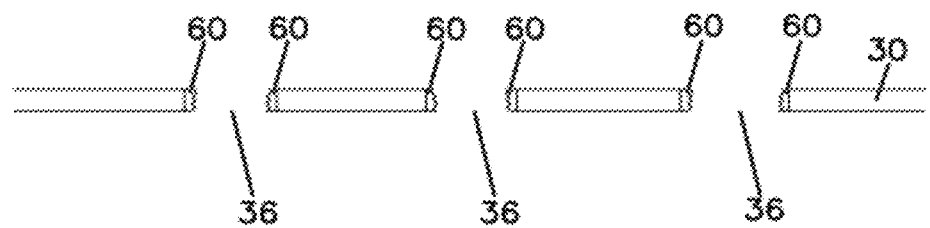

In an embodiment, in the contracted state, the opening(s) 36 in the outer expandable and collapsible structure 30 is closed by a scissile plug 60 (FIG. 7A). The dilated state of this embodiment is schematically represented in FIG. 7B which shows the openings 36.

In an embodiment, the outer expandable and collapsible structure 30 is made of a material in which the openings 36 are pores 48 that, in the contracted state, are too small to provide transit for the benefit composition 14. Application of the radially outward force both can open the pores 48 and, in an embodiment, urge the benefit composition 14 through the pores 48. For example, a the outer expandable and collapsible structure 30 can be made of a crosslinked polymeric material of a variable degree of crosslinking at positions in the material. A pore 48 can form at a position in the material where the degree of crosslinking is sufficiently low. A major portion of the outer expandable and collapsible structure 30 has a degree of crosslinking sufficient to maintain the integrity of the structure.

Inner Balloon

The inner balloon of the device can be formed from any material, or combination of materials, capable of expanding, and suitable for use within the body. The one or more material(s) can be based on use of the device. In an embodiment, the inner balloon is made of a material that can be folded in the contracted state to fit within the device and that can unfold as the device moves toward the dilated state. Such an inner balloon can be made of an elastomeric material or a material that is not elastomeric. The inner balloon can be less elastic than the outer balloon.

In an embodiment, the inner balloon is made of a material that is a compliant and flexible material, such as an elastomer (a polymer with elastic properties). Elastomers are typically thermoplastic polymers. Suitable elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The inner balloon can be made of a single elastomeric material, or a combination of materials. The inner balloon structure can be manufactured by an extrusion process, so that the elastic structure is a single layer of material, or co-extruded to form a multi-layered material. The inner balloon can have a thickness suitable for the desired application and device. For example, the thickness of an elastic structure can be in the range of about 5 μm to about 100 μm. The manufacture of expandable and collapsible structures is well known in the art, and any suitable process can be carried out to provide the expandable substrate portion of the insertable medical device as described herein. The inner balloon can be made of material that is not permeable (e.g., to the therapeutic composition).

The inner balloon can be textured. Texture on the inner balloon can provide advantages such as one or more of increased load when folded, ease of manufacture, and retention of the therapeutic composition.

Reservoir

The reservoir containing the therapeutic composition can be any of a variety of predetermined sizes. A reservoir of predetermined size can allow for accurate delivery of a predetermined dose or amount of the therapeutic agent. In an embodiment, the reservoir is in fluid communication with a third lumen reservoir. A third lumen reservoir can provide additional capacity for providing a larger amount of therapeutic agent than can be accommodated in the volume of the reservoir between the inner and outer balloons.

Outer Balloon

The outer balloon can be made from any of a variety of materials and be in any of a variety of configurations suitable for delivery of the therapeutic composition. In an embodiment, the outer balloon protects the reservoir, e.g., from releasing the therapeutic composition before it reaches the desired site. It can be made of a material that is elastomeric or non-elastomeric. In an embodiment, it has some recoil to avoid problems removing the device, e.g., from a site in a blood vessel. The outer balloon can be made from an elastic or tearable material, e.g., silicone. Other suitable materials include the materials described above for the inner balloon. The exterior of the outer balloon can be lubricious.

Apertures

The aperture(s) can be in any of a variety of configurations. In addition, any of a variety of mechanisms can be used to close and/or open the apertures. The open apertures can define any of a variety of shapes in any of a variety of sizes. In an embodiment, the apertures are macroscopic and the therapeutic composition can flow through them without force being applied (e.g., diffusion of a solution or solute through the aperture). In an embodiment, the apertures are sufficiently small that force must be applied to move the therapeutic composition through them (e.g., a viscous therapeutic composition forced through "pin holes").

Aperture Seal Material

The aperture can be sealed by any of a variety of materials. These materials can form the scissile layer 54 or 56, patch 58, or plug 60. Suitable materials include those described below.

Wax Seal Material

The present aperture seal material can be a wax composition that includes a wax, a mixture of waxes, or a mixture of one or more waxes with other materials such as other lipids. The wax seal material can, for example, be solid (e.g., waxy or paste-like) or semi-solid at the body temperature of a subject. In an embodiment, the wax seal material includes a wax with a melting point of about 50 to about 100° C. In an embodiment, the wax seal material includes a wax with a melting point of about 50 to about 70° C.

The wax can be a single wax or a mixture of waxes. The wax can be an ester (e.g., an ester of a monohydroxy alcohol), a fatty acid, an alcohol, a hydrocarbon, a natural or hydrogenated oil, or a mixture thereof. Suitable waxes include: a plant derived wax such as carnauba wax, candelilla wax, bayberry (or myrtle) wax, Japan wax, or a mixture thereof; a wax of animal origin such as beeswax, wool wax (e.g., lanolin), spermaceti, Chinese wax, or a mixture thereof; a mineral wax such as ozocerite, paraffin, or a mixture thereof; or a mixture thereof.

Suitable waxes include carnauba wax, candelilla wax, spermaceti, bees wax, montan wax, microcrystalline wax, lecithin, hydrogenated tallow, paraffin wax, cetyl alcohol, cetostearyl alcohol, stearic acid hydrogenated vegetable oil, such as hydrogenated cottonseed oil, hydrogenated soybean oil, glyceryl behenate, glyceryl palmitostearate, shellac wax, petrolatum, or a mixture thereof. Suitable waxes include synthetic waxes, e.g., polyethylene, and the like. Suitable waxes include hydrogenated vegetable oil, carnauba wax, candelilla wax, spermaceti, beeswax, montan wax, microcrystalline wax, lecithin, hydrogenated tallow, paraffin wax, shellac wax, petrolatum, glyceryl behenate, glyceryl palmitostearate, cetyl alcohol, cetostearyl alcohol, stearic acid, polyethylene, or a mixture thereof.

A textured surface of the outer balloon can aid in retaining the wax seal material on the device. A device including a wax seal can be made by filling the reservoir with a liquid composition of a therapeutic agent followed by dipping the device in melted wax to apply the wax to the surface of the outer balloon.

The melting point of the present wax seal material can be determined by any one of a variety of art accepted methods. Suitable methods include the Mettler drop point test (see, e.g., ASTM D 3954). Briefly, in this test the sample to be measured is placed in a cup and heated at a given rate. The temperature at which a drop of molten material passes through a standard orifice is recorded. Other methods include the AOCS Method Cc 2-38 (the Wiley melting point), open capillary slip point, and the softening point tests.

Embodiments of Cross-Linking Aperture Seals

A linking agent suitable for use in the present aperture seal material is described in U.S. Pat. No. 5,414,075, the disclosure of which is incorporated herein by reference.

This material includes a chemical backbone having attached to it one or more first latent reactive groups and one or more second latent reactive groups, each of the first and second latent reactive groups being attached to the backbone in such a manner that, upon activation of the latent reactive groups in the presence of a support surface, a) the first latent reactive groups are capable of covalently bonding to the support surface, and b) upon bonding of the first latent reactive groups to the surface, the second latent reactive groups are; i) restricted from reacting with either a spacer or the support surface, ii) capable of reverting to their inactive state, and iii) upon reverting to their inactive state, are thereafter capable of being reactivated in order to later bind a target molecule, thereby attaching the target molecule to the surface.

In a particularly preferred embodiment, the chemical backbone of such a multifunctional reagent is a single tetrahedral carbon atom. Attached to the central carbon, in this embodiment, are four identical latent reactive groups, in the form of photoreactive groups, each attached via identical spacer chains. Upon exposure to a suitable light source, each of the latent reactive groups are subject to activation.

By virtue of conformational and/or steric constraints that the reagent imposes on itself (hence "restrained"), both by the tetrahedral nature of the central carbon, as well as the physical-chemical nature of the spacer chains themselves (e.g., their length, reactivity, and flexibility), the reagent is restricted, in that a maximum of three of the four activated latent reactive groups on any given preferred reagent molecule are able to attach to the support surface. The remaining unreacted group(s) are thus able to revert to their inactive state. In a subsequent step, the unreacted group(s) can be reactivated in the presence of a target molecule, in order to covalently bond the target molecule to the surface.

The reagent of the present invention involves a chemical backbone having attached to it one or more first latent reactive groups capable of attaching to a surface, and one or more second latent reactive groups capable of attaching to a target molecule intended for immobilization. Chemically, the first and second latent reactive groups, and respective spacers, can be the same or different.

In situations in which all latent reactive groups and spacers are chemically, or at least functionally, the same, the distinction between first and second latent reactive groups may actually be accomplished at the time of the first activation step, i.e., those groups that are activated and attach to the surface will be considered "first" latent reactive groups, and those that remain unreacted (whether or not they have been activated) will be considered "second" latent reactive groups.

The first and second latent reactive groups are preferably attached to the backbone by spacer chains in such a manner that, upon activation of the latent reactive groups in the presence of a support surface, the first latent reactive groups are capable of covalently bonding to the surface. The second latent reactive groups are thereby conformationally restricted, thus preventing reaction with either their spacers, other restricted reagents of the same type, or the support surface. In addition, after the first activation step and removal of the activating stimulus (e.g., illumination source), the second latent reactive groups are capable of reverting to their inactive state and can thereafter be activated (or reactivated, as the case may be) to covalently bond a target molecule.

The following diagram depicts the concept of the preferred tetrahedral core structure, as exemplified by the empirical formula $X(Y)_4(Z)_4$, shown below as Formula I:

FORMULA I

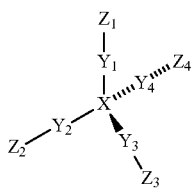

In Formula I:
X=the chemical backbone;
$Y_1, Y_2, Y_3, Y_4$=optional spacers; and
$Z_1, Z_2, Z_3, Z_4$=latent reactive groups.

In an embodiment, the invention provides a core molecule containing four dimethyleneoxy groups bonded as spacers to a central tetrahedral carbon atom, the carbon atom serving in this instance as the chemical backbone. The backbone, spacers, and latent reactive groups are described herein, for the sake of simplicity, as being distinct portions of the reagent of the present invention. In the chemical synthesis of a reagent however, these portions will rarely be provided as three independent precursors. Instead, and most often, the portion referred to herein as the spacer will be formed as the result of the reaction between two molecules, one that contains the core molecule and another that contains the latent reactive group.

By virtue of the physical and chemical properties of the photoreactive groups and the methylene group spacers, together with the conformational restrictions provided by the tetrahedral carbon backbone, the reagent is able to attach up to three of its photoreactive groups to a surface upon photoactivation. Being conformationally restricted, and thus unable to interact with the support surface or the spacers, any remaining photoreactive group(s) are able to return to their inactive states upon removal of fight, once again being capable of activation by subsequent illumination.

In addition to reagents of the particularly preferred embodiment, containing a central carbon atom, reagents of the present invention can be prepared having any suitable chemical (e.g., organic and/or inorganic) backbone structure, including those that employ a single atom, such as silicon, nitrogen, phosphorus, and any other atom with four or more bonds nonplanar with respect to one another.

Also, molecules having conformationally restricted ring structures (such as inositol, i.e., hexahydroxy cyclohexane) can be derivatized with latent reactive groups in a manner analogous to that described herein for pentaerythritol, to provide latent reactive groups in both axial and equatorial positions. Other polyhydroxylated compounds such as mono- and di-saccharides, and cyclodextrins, are suitable as well, in that they offer alternative opportunities to create other multisubstituted reagents having varying placements and densities of latent reactive groups.

Contact with a support surface and activation of the latent reactive groups will result in covalent bond formation through at least one latent reactive group, with at least one other latent reactive group being conformationally restricted and thus unable to react at the surface.

Spacers useful in the reagent of the present invention can be bonded to the tetrahedral atom and can be of any suitable length and structure. A "spacer", as used herein, refers to that region of a reagent between a latent reactive group and a chemical backbone. The use of spacers is optional, and would not be necessary, for instance, for such compounds as acylated derivatives of tetraphenylmethane having the structure shown below as Formula II:

FORMULA II

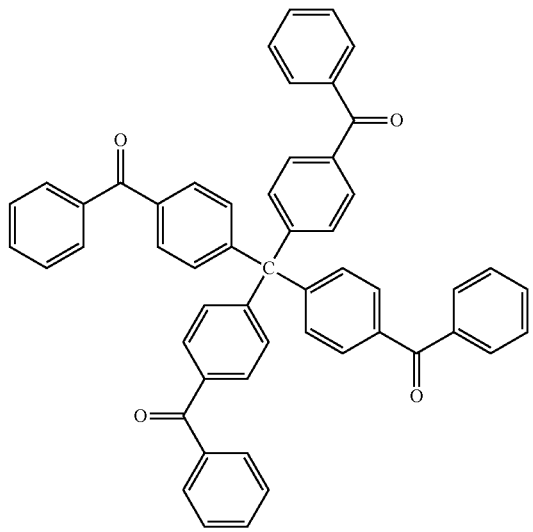

A "latent reactive group", as used herein, refers to a chemical group that responds to an applied external energy source in order to undergo active specie generation, resulting in covalent bonding to an adjacent chemical structure (e.g., an abstractable hydrogen). Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones such as acetophenone and benzophenone, or their derivatives, are preferred, since these functional groups, typically, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are suitable.

A linking agent suitable for use in the present aperture seal material is described in U.S. Pat. No. 5,714,360, the disclosure of which is incorporated herein by reference.

A chemical linking agent including a di- or higher functional photoactivatable charged compound can be employed as an aperture seal. This linking agent provides at least one group that is charged under the conditions of use in order to provide improved water solubility. The agent further provides two or more photoactivatable groups in order to allow the agent to be used as a cross-linking agent in aqueous systems.

In an embodiment, the charge is provided by the inclusion of one or more quaternary ammonium radicals, and the photoreactive groups are provided by two or more radicals of an aryl ketone such as benzophenone.

In a preferred embodiment, the invention provides a linking agent of the general formula: X—Y—X; wherein each X, independently, is a radical containing a photoreactive group and Y is a radical containing, inter alia, one or more charged groups. In such an embodiment, the number and/or type of charged group(s) is sufficient to provide the molecule with sufficient aqueous solubility to allow the agent to be used (i.e., applied to a surface and activated) in a solvent system having water as a major component.

In an embodiment, Y contains one or more nitrogen-containing (e.g., quaternary ammonium) groups. For example, Y contains a linear or heterocyclic radical selected from the group consisting of:

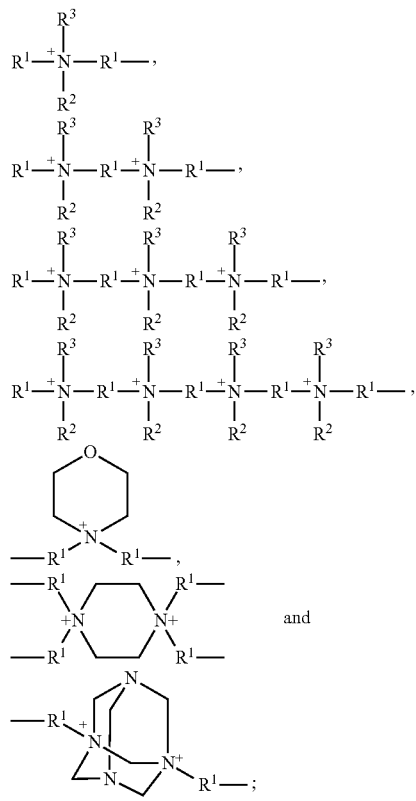

wherein each $R^1$ independently is a radical containing an alkylene, oxyalkylene, cycloalkylene, arylene, or aralkylene group, each $R^2$ independently is a radical containing an alkyl, oxyalkyl, cycloalkyl, aryl, or aralkyl group, and each $R^3$ independently is either a non-bonding pair of electrons, a hydrogen atom, or a radical of the same definition as $R^2$, in which the $R^1$, $R^2$ and $R^3$ groups can contain noninterfering heteroatoms such as O, N, S, P and the like, and/or noninterfering substituents such as halo (e.g., Cl) and the like.

In an embodiment, one or more $R^2$ radicals contains an aralkyl group in the form of a photoactivatable aryl ketone. These groups, in addition to the two photoactivatable groups provided by the above-defined X groups, can be used to provide the "triphoto", "tetraphoto" and higher order photoactivatable groups described herein. The use of three or more total photoreactive groups provides the linking agent with further ability to cross-link the agent to a target molecule and/or to a surface.

In yet another preferred embodiment, the $R^2$ and $R^3$ groups of the above linear radicals can, in effect, be fused (e.g., an $R^2$ and an $R^3$ on a single N atom, or a suitable combination of $R^2/R^3$ groups on adjacent N atoms) in order to form heterocyclic structures other than those exemplified above. The specific choice and relationship between R groups in a linking agent of the present invention is not critical, so long as the linking agent provides two or more photoactivatable groups and retains sufficient water solubility for its intended use.

Degradable Linking Agent

A water-soluble, degradable linking agent suitable for use as the present aperture seal material is described in U.S. Patent Application No. 61/319,127, the disclosure of which is incorporated herein by reference.

The degradable linking agent can have the formula $Photo^1$-LG-$Photo^2$, wherein $Photo^1$ and $Photo^2$, independently, represent at least one photoreactive group and LG represents a linking group. In one embodiment, one or more photoreactive groups include an aryl ketone. In a more particular embodiment, one or more photoreactive groups include benzophenone.

In one embodiment, the linking group includes one or more silicon atoms or one or more phosphorus atoms, wherein each photoreactive group is independently bound to the linking group by a covalent linkage that includes at least one heteroatom. In one embodiment, at least one heteroatom is selected from oxygen, nitrogen, selenium, sulfur, or a combination thereof. In one embodiment, at least one photoreactive group, heteroatom and linking group form an ether or an amine.

In a more particular embodiment, the linking group includes one silicon atom covalently bound to at least two photoreactive groups. In another embodiment, the linking group includes at least two silicon atoms. In another embodiment, the linking group has the formula Si—Y—Si, wherein Y represents a linker that can be null, an amine, ether, linear or branched $C_1$-$C_{10}$ alkyl, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30.

In another embodiment, the linking group includes one or more phosphorester bonds and/or one or more phosphoramide bonds wherein one or more phosphorester and/or one or more phosphoramide bonds form a covalent bond with at least one photoreactive group, such that the linking group includes at least two photoreactive groups. In one embodiment, the linking group is covalently attached to three photoreactive groups, wherein each photoreactive group is covalently bound to the linking group by a phosphorester or phosphoramide bond. In another embodiment, the linking group includes at least one phosphorus atom with a phosphorus-oxygen double bond (P=O), wherein at least one photoreactive group is bound to at least one phosphorus atom. In yet another embodiment, the linking group includes one phosphorus atom with a phosphorus-oxygen double bond (P=O), wherein at least two or three photoreactive groups are covalently bound to the phosphorus atom. In another embodiment, the linking group includes at least two phosphorus atoms, wherein at least one phosphorus atom includes a phosphorus-oxygen double bond (P=O), and at least one or at least two photoreactive groups are covalently bound to each phosphorus atom.

The degradable linking agent includes one or more photoreactive groups and a linking group, wherein each photoreactive group is independently attached to the linking group by a degradable linkage. In other embodiments, the degradable linking agent includes two or more photoreactive groups. In still other embodiments, the degradable linking agent includes three or more photoreactive groups.

The degradable linking agent includes one or more photoreactive groups attached to a linking group. The degradable linking agent can be represented by the formula Photo$^1$-LG-Photo$^2$, wherein Photo$^1$ and Photo$^2$ independently represent at least one photoreactive group and LG represents a linking group. The term "linking group" as used herein, refers to a segment or group of molecules configured to connect two or more molecule to each another, wherein the linking group is capable of degrading under one or more conditions. In one embodiment, the linking group includes at least one silicon atom. In another embodiment, the linking group includes at least one phosphorus atom.

The term "degradable linking group" as used herein, refers to a moiety configured to connect one molecule to another, wherein the linking group is capable of cleavage under one or more conditions. The term "biodegradable" as used herein, refers to degradation in a biological system, and includes for example, enzymatic degradation or hydrolysis. It should be noted that the term "degradable" as used herein includes both enzymatic and non-enzymatic (or chemical) degradation. It is also understood that hydrolysis can occur in the presence of or without an acid or base. In one embodiment, the linking agent is water soluble. In another embodiment, the linking agent is not water soluble.

In addition to providing a degradable bond, the linking group can function as a spacer, for example, to increase the distance between the photoreactive groups of the linking agent. For example, in some instances it may be desirable to provide a spacer to reduce steric hindrance that may result between the photoreactive groups, which could interfere with the ability of the photoreactive groups to form covalent bonds with a support surface, or from serving as a photoinitiator for polymerization. As described herein, it is possible to vary the distance between the photoreactive groups, for example, by increasing or decreasing the spacing between one or more photoreactive groups.

As described herein, one or more photoreactive groups can be bound to a linking group by a degradable linkage. In one embodiment, the degradable linkage between the photoreactive group and the linking group includes at least one heteroatom, including, but not limited to oxygen, nitrogen, selenium, sulfur or a combination thereof. In one embodiment, a photoreactive group, linking group and heteroatom form an ether ($R^1$—O—$R^2$), wherein $R^1$ is a photoreactive group and $R^2$ is a linking group. In another embodiment, a photoreactive group, linking group and heteroatom form an amine,

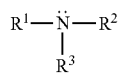

wherein $R^1$ is a photoreactive group, $R^2$ is a linking group, and $R^3$ is hydrogen, aryl or alkyl, a photoreactive group, or a hydroxyl or salt thereof. In one embodiment, $R^3$ is cyclic, linear or branched, saturated or unsaturated, aromatic or heteroaromatic, or a combination thereof. The stability of the ether and/or amine linkage can be influenced depending upon the size (e.g., chain length, branching, bulk, etc.) of the substituents. For example, bulkier substituents will generally result in a more stable linkage (i.e., a linking agent that is slower to degrade in the presence of water and/or acid).

In one embodiment, the linking group includes one or more silicon atoms. In a particular embodiment, the linking group includes one silicon atom (which can be referred to as a monosilane) covalently bound to at least two photoreactive groups. In another embodiment, the linking group includes at least two silicon atoms (which can be referred to as a disilane). In one embodiment, the linking group can be represented by the formula Si—Y—Si, wherein Y represents a linker that can be null (e.g., the linking group includes a direct Si—Si bond), an amine, ether, linear or branched $C_1$-$C_{10}$ alkyl, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. One embodiment of a disilane linking agent is shown below

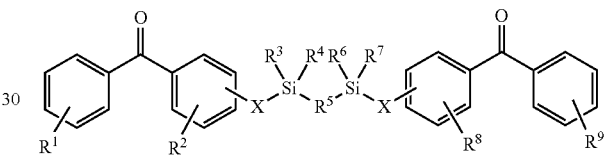

wherein $R^1$, $R^2$, $R^8$ and $R^9$ can be any substitution, including, but not limited to H, alkyl, halide, hydroxyl, amine, or a combination thereof; $R^3$, $R^4$, $R^6$ and $R^7$ can be alkyl, aryl or a combination thereof; $R^5$ can be any substitution, including but not limited to O, alkyl or a combination thereof; and each X, independently, can be O, N, Se, S, or alkyl, or a combination thereof. One specific embodiment is shown below:

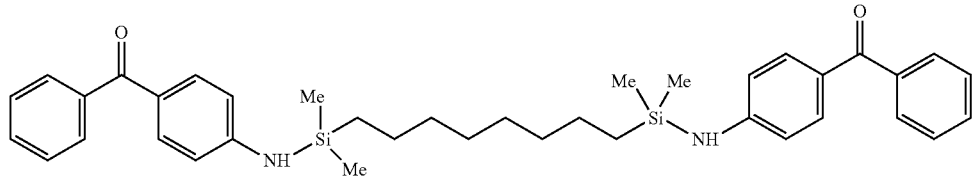 [SMILES: C[Si](C)(CCCCCCCC[Si](C)(C)Nc1ccc(C(=O)c2ccccc2)cc1)Nc1ccc(C(=O)c2ccccc2)cc1]

In one embodiment, the degradable linking agent can be represented by the formula

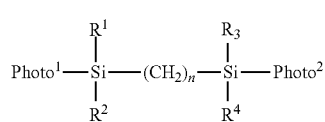

wherein Photo$^1$ and Photo$^2$, independently, represent one or more photoreactive groups and n is an integer between 1 and 10, wherein the degradable linking agent comprises a covalent linkage between at least one photoreactive group and the linking group, wherein the covalent linkage between at least one photoreactive group and the linking group is interrupted by at least one heteroatom. In general, a longer hydrocarbon chain between the two silicon atoms will tend to increase the flexibility of the linking agent and may facilitate crosslinking between a greater number of polymers than a linking agent with a shorter carbon chain, since the photoreactive groups can react with polymers located farther apart from one another. In the formula shown above, $R^1$, $R^2$, $R^3$, $R^4$ are independently alkyl or aryl, including, but not limited to cyclic, linear or branched, saturated or unsaturated, aromatic or heteroaromatic, or a combination thereof. In a more particular embodiment, $R^1$-$R^4$ are independently phenyl, methyl, ethyl, isopropyl, t-butyl, or a combination thereof. In another embodiment, $R^1$-$R^4$ can also be, independently, a photoreactive group. In yet another embodiment, $R^1$-$R^4$ can also be, independently, hydroxyl or salt thereof. In one embodiment, the hydroxyl salt includes a counterion that is lithium, sodium, potassium, or a combination thereof.

In another embodiment, the linking agent can be represented by the formula

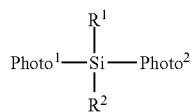

wherein $Photo^1$ and $Photo^2$, independently, represent one or more photoreactive group, wherein the degradable linking agent comprises a covalent linkage between at least one photoreactive group and the linking group, wherein the covalent linkage between at least one photoreactive group and the linking group is interrupted by at least one heteroatom; $R^1$ and $R^2$ are independently alkyl or aryl, including, but not limited to cyclic, linear or branched, saturated or unsaturated, aromatic or heteroaromatic, or a combination thereof. In a more particular embodiment, $R^1$ and $R^2$ are independently phenyl, methyl, ethyl, isopropyl, t-butyl, or a combination thereof. $R^1$ and $R^2$ can also be, independently, a photoreactive group, wherein the degradable linking agent comprises a covalent linkage between at least one photoreactive group and the linking group, wherein the covalent linkage between at least one photoreactive group and the linking group is interrupted by at least one heteroatom; or hydroxyl or salt thereof. In one embodiment, the hydroxyl salt includes a counterion that is lithium, sodium, potassium, or a combination thereof. One embodiment of a monosilane linking agent is shown below

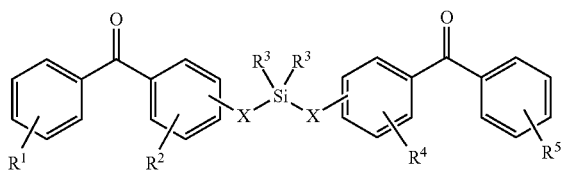

in which $R^1$ and $R^5$ can be any substitution, including, but not limited to H, halogen, amine, hydroxyl, alkyl, or a combination thereof; $R^2$ and $R^4$ can be any substitution, except OH, including, but not limited to H, alkyl or a combination thereof; $R^3$ can be alkyl, aryl or a combination thereof; and X, independently, can be O, N, Se, S, alkyl or a combination thereof.

In another embodiment, the linking group includes one or more phosphorous atoms. In one embodiment, the linking group includes one phosphorus atom (which can also be referred to as a mono-phosphorus linking group). In another embodiment, the linking agent includes two phosphorus atoms (which can also be referred to as a bis-phosphorus linking group). In one embodiment, the linking group comprises at least one phosphorus atom with a phosphorus-oxygen double bond (P=O), wherein at least one or two photoreactive groups are bound to the phosphorus atom. In another embodiment, the linking group comprises one phosphorus atom with a phosphorus-oxygen double bond (P=O), wherein two or three photoreactive groups are covalently bound to the phosphorus atom. In another embodiment, the linking group comprises at least two phosphorus atoms, wherein at least one phosphorus atom includes a phosphorus-oxygen double bond (P=O), and at least one or two photoreactive groups are covalently bound to each phosphorus atom.

In a more particular embodiment, the linking agent can be represented by the formula:

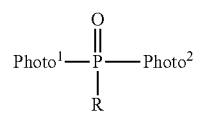

wherein $Photo^1$ and $Photo^2$, independently, represent one or more photoreactive groups, wherein the degradable linking agent comprises a covalent linkage between at least one photoreactive group and the linking group, wherein the covalent linkage between at least one photoreactive group and the linking group is interrupted by at least one heteroatom and R is alkyl or aryl, a photoreactive group, hydroxyl or salt thereof; or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the degradable linking agent can be represented by formula:

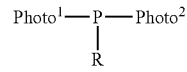

wherein $Photo^1$ and $Photo^2$ independently, represent one or more photoreactive groups, wherein the degradable linking agent comprises a covalent linkage between at least one photoreactive group and the linking group, wherein the covalent linkage between at least one photoreactive group and the linking group is interrupted by at least one heteroatom and R is alkyl or aryl, a photoreactive group (wherein the covalent linkage between the photoreactive group and the linking group may be interrupted by at least one heteroatom), hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, R is phenyl, methyl, ethyl, isopropyl, t-butyl, or a combination thereof.

In another embodiment, the degradable linking agent can be represented by the formula:

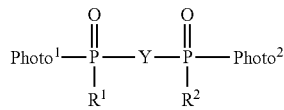

wherein Photo$^1$ and Photo$^2$, independently, represent one or more photoreactive groups, wherein the degradable linking agent comprises a covalent linkage between at least one photoreactive group and the linking group, wherein the covalent linkage between at least one photoreactive group and the linking group is interrupted by at least one heteroatom; Y represents a linker that can be null (i.e., not present, such that the linking group includes a direct P—P bond), N or O, linear or branched $C_1$-$C_{10}$ alkyl, or a combination thereof; and $R^1$ and $R^2$ are independently alkyl, aryl, a photoreactive group (wherein the covalent linkage between the photoreactive group and the linking group can be interrupted by at least one heteroatom), hydroxyl or salt thereof, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof. In general, a longer hydrocarbon chain between the two phosphorus atoms will tend to increase the flexibility of the linking agent and may facilitate crosslinking between a greater number of polymers than a linking agent with a shorter carbon chain, since the reactive photoreactive groups can react with polymers located farther apart from one another. In one embodiment, Y can be O, $CH_2$, $OCH_2CH_2O$ and $O(CH_2CH_2O)_n$ wherein n is an integer between 1 and 5, between 1 and 10, between 1 and 15, between 1 and 20, between 1 and 25, or between 1 and 30. One embodiment is shown below

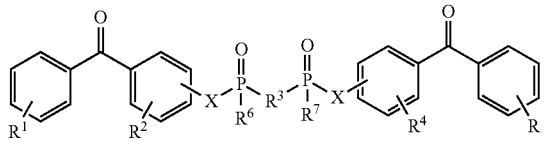

in which $R^1$, $R^2$, $R^4$ and $R^5$ can be any substitution, including but not limited to H, alkyl, halogen, amine, hydroxyl, or a combination thereof; $R^3$ can be any substitution, including but not limited to O, alkyl, or a combination thereof; and each X can independently be O, N, Se, S, alkyl, or a combination thereof. In one embodiment, the linking agent includes one or more phosphorester bonds and one or more phosphoramide bonds, and can be represented by the formula:

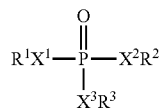

wherein X and $X^2$ are, independently, O, N, Se, S or alkyl; $R^1$ and $R^2$ are independently, one or more photoreactive groups, and $X^3$ is O, N, Se, S, alkyl or aryl; $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or a hydroxyl or salt thereof. In one embodiment, the hydroxyl salt counterion is lithium, sodium, potassium, or a combination thereof.

In one embodiment, the linking agent comprises a triphosphorester, which can be represented by the formula.

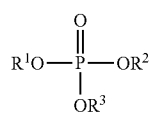

wherein $R^1$ and $R^2$ are independently, one or more photoreactive groups, and $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or a hydroxyl or salt thereof. In one embodiment, the hydroxyl salt counterion is lithium, sodium, potassium, or a combination thereof.

In another embodiment, the linking agent comprises a triphosphoramide, which can be represented by the formula.

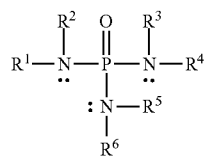

wherein $R^1$-$R^6$ are independently, a photoreactive group, a hydroxyl or salt thereof, alkyl or aryl, or a combination thereof, wherein at least two of $R^1$-$R^6$ are, independently, a photoreactive group. In one embodiment, the hydroxyl salt counterion is lithium, sodium, potassium, or a combination thereof. In a more particular embodiment, $R^1$-$R^6$ are independently cyclic, linear or branched, saturated or unsaturated, aromatic or heteroaromatic, or a combination thereof. In a more particular embodiment, $R^1$-$R^6$ are, independently, phenyl, methyl, ethyl, isopropyl, t-butyl, or a combination thereof.

The degradable linking agent can be formed using any suitable reaction pathway. In one embodiment, the degradable linking agent is formed by reacting a functionalized linking element with one or more, typically two or more photoreactive groups. As used herein, the term "linking element" refers to the linking group component of the degradable linking agent before it is bonded to one or more photoreactive groups. The term "functionalized linking element" is used to indicate that the linking element includes one or more reactive functional groups. In one embodiment, the linking element includes one or more halogen functional groups. The term "halogen" refers to fluorine, chlorine, bromine, or iodine functional groups. In another embodiment, the linking element includes one or more trifluoromethanesulfonate ($CF_3SO_3$—) functional groups.

In one embodiment, the linking element includes one or more silicon atoms. In one embodiment, the linking element includes one or more halogen substituents, such as fluorine, chlorine, bromine, iodine, and combinations thereof. In another embodiment, the linking element includes at least two halogen substituents. In another embodiment, the linking element includes one or more trifluoromethanesulfonate (triflate) substituents. In another embodiment, the linking element includes at least two triflate substituents. In a more particular embodiment, the linking element includes one silicon atom with at least two halogen or triflate substituents. In another embodiment, the linking element includes at least two silicon atoms. In a more particular embodiment, the linking element includes two silicon atoms, wherein each silicon atom includes at least one halogen or triflate substituent. In one embodiment, the linking element can be represented by the formula Si—Y—Si, wherein Y represents a linker that can be null, an amine, ether, linear or branched $C_1$-$C_{10}$ alkyl, or a combination thereof, wherein each silicon atom includes at least one halogen or triflate substituent. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30.

In one embodiment, the linking element can be represented by the formula

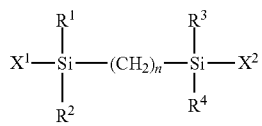

wherein $X^1$ and $X^2$ are independently halogen, such as fluorine, chlorine, bromine, iodine; trifluoromethanesulfonate; or a combination thereof and n is an integer between 1 and 10. $R_1$-$R_4$ are independently alkyl or aryl, including, but not limited to cyclic, linear or branched, saturated or unsaturated, aromatic or heteroaromatic, or a combination thereof. In a more particular embodiment, $R^1$-$R^4$ are independently phenyl, methyl, ethyl, isopropyl, t-butyl, or a combination thereof. In another embodiment, $R^1$-$R^4$ can also be, independently, halogen. In yet another embodiment, $R^1$-$R^4$ can also be, independently, hydroxyl or salt thereof. In one embodiment, the hydroxyl salt includes a counterion that is lithium, sodium, potassium, or a combination thereof.

In another embodiment, the linking element can be represented by the formula

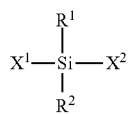

wherein $X^1$ and $X^2$ are independently halogen; such as fluorine, chlorine, bromine, and iodine; or trifluoromethanesulfonate; $R^1$ and $R^2$ are independently alkyl or aryl, including, but not limited to cyclic, linear or branched, saturated or unsaturated, aromatic or heteroaromatic, or a combination thereof. In a more particular embodiment, $R^1$ and $R^2$ are independently phenyl, methyl, ethyl, isopropyl, t-butyl, or a combination thereof. $R^1$ and $R^2$ can also be, independently, halogen, hydroxyl or hydroxyl salt. In one embodiment, the hydroxyl salt includes lithium, sodium, potassium, or a combination thereof as a counterion.

In another embodiment, the linking element includes one or more phosphorous atoms. In one embodiment, the linking element comprises at least one phosphorus atom with a phosphorus-oxygen double bond (P=O), wherein at least one halogen or trifluoromethanesulfonate substituent is bound to at least one phosphorus atom. In another embodiment, the linking element comprises one phosphorus atom with a phosphorus-oxygen double bond (P=O), wherein two or three halogen or trifluoromethanesulfonate substituents are, independently, covalently bound to the phosphorus atom. In another embodiment, the linking element comprises at least two phosphorus atoms, wherein at least one phosphorus atom includes a phosphorus-oxygen double bond (P=O), and at least one or two halogen or trifluoromethanesulfonate substituents are covalently bound to each phosphorus atom. In a more particular embodiment, the linking element comprises two phosphorus atoms.

In a more particular embodiment, the linking element can be represented by the formula

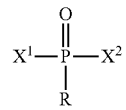

wherein $X^1$ and $X^2$ are independently halogen; such as fluorine, chlorine, bromine, and iodine; or trifluoromethanesulfonate; and R is alkyl or aryl, halogen, hydroxyl or a hydroxyl salt, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the degradable linking element can be represented by formula:

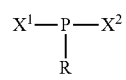

wherein $X^1$ and $X^2$ are independently halogen, such as fluorine, chlorine, bromine, and iodine; or trifluoromethanesulfonate and R is alkyl or aryl, halogen, trifluoromethanesulfonate, hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, $R^1$ and $R^2$ are independently phenyl, methyl, ethyl, isopropyl, t-butyl, or a combination thereof.

In another embodiment, the degradable linking element can be represented by the formula:

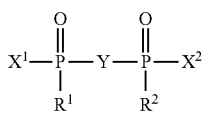

wherein $X^1$ and $X^2$ are independently halogen, such as fluorine, chlorine, bromine, and iodine; or trifluoromethanesulfonate, Y represents a linker that can be null, an amine, an ether, linear or branched $C_1$-$C_{10}$ alkyl, or a combination thereof; and $R^1$ and $R^2$ are independently alkyl, aryl, halogen, hydroxyl or salt thereof, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof.

Water-Soluble, Degradable Linking Agent

A water-soluble, degradable linking agent suitable for use in the present polymeric aperture seal material is described in U.S. Patent Application Nos. 61/285,345 and 61/358,464, the disclosure of which is incorporated herein by reference.

Described in this section is a linking agent that includes a core molecule with one or more charged groups; and one or more photoreactive groups covalently attached to the core molecule by one or more degradable linkers. In one embodiment, the linking agent includes a non-polymeric core molecule. In one embodiment, the non-polymeric core molecule is a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof. In one embodiment, one or more degradable linkers comprise an amide, an ester, a thiocarbamate, or a combination thereof. In one embodiment, one or more photoreactive group is an aryl ketone, including, for example, acetophenone, benzophenone, anthraquinone, anthrone, anthrone-like heterocycles, substituted derivatives thereof, or a combination thereof. In one embodiment, one or more charged groups are negatively charged, including, for example, an organic acid selected from sulfuric acid, sulfonic acid, carboxylic acid, phosphoric acid, phosphonic acid, or a combination thereof. In another embodiment, one or more charged groups are positively charged, for example, a quaternary ammonium salt.

Described herein is a water-soluble, degradable linking agent. The degradable linking agent includes one or more photoreactive groups, one or more charged groups, and one or more degradable linkers configured to operably attach one or more photoreactive groups to one or more negatively charged groups. In one embodiment, the linking agent includes a core having one or more charged groups attached directly or indirectly thereto and one or more photoreactive groups attached to the non-polymeric core by one or more degradable linkers.

The degradable linking agent includes one or more photoreactive groups attached to one or more charged groups by a degradable linker. In a more particular embodiment, the degradable linking agent includes a core molecule to which the charged groups and the photoreactive groups can be independently attached. In one embodiment, the degradable linking agent includes a non-polymeric core molecule. The term "degradable linker" as used herein, refers to a segment configured to connect one part of the linking agent to another, wherein the linker is capable of cleavage under one or more conditions. The term degradable as used herein also encompasses "biodegradable linkers." The term "biodegradable" as used herein, refers to degradation in a biological system, and includes for example, enzymatic degradation or hydrolysis. It should be noted that the term "degradable" as used herein includes both enzymatic and non-enzymatic (or chemical) degradation. In one embodiment, the degradable linker comprises one or more degradable linkages such as an amide, an ester, a thiocarbamate, or combinations thereof.

In addition to providing a degradable segment, the degradable linker can function as a spacer, to increase the distance between one or more photoreactive groups and the core molecule. For example, in some instances it may be desirable to provide a spacer to reduce steric hindrance that may result between the core molecule and one or more photoreactive groups that could interfere with the ability of one or more photoreactive groups to form covalent bonds with a support surface, or from serving as a photoinitiator for polymerization. As described herein, it is possible to vary the distance between the photoreactive groups, for example, by increasing or decreasing the spacing between one or more photoreactive groups.

A degradable linking agent can be represented by the formula:

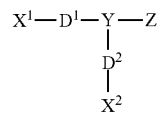

wherein $X^1$ and $X^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $D^1$ and $D^2$ are, independently, degradable segments, including, for example, degradable segments that include an amide, an ester, a thiocarbamate, or a combination thereof; Y represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof; and Z represents one or more charged groups, including, for example, one or more negatively charged groups such as an organic acid salt, including but not limited to sulfuric acid, sulfonic acid, carboxylic acid, phosphoric acid, phosphonic acid, or a combination thereof; one or more positively charged groups, for example, a quaternary ammonium salt, or a combination thereof.

In the formula shown above, the two or more photoreactive groups ($X^1$ and $X^2$) are discrete. As used herein, the term "discrete" means that the two or more photoreactive groups are distinct from each other, as compared to a bifunctional photoreactive agent, that can include two or more photoreactive moieties, such as a conjugated cyclic diketone wherein each ketone group of the diketone is adapted to serve as a photoreactive moiety capable of being activated in order to provide a free radical. It is also understood that the first and second photoreactive groups and/or the first and second degradable linkers may or may not be the same. For example, in one embodiment, the photoreactive groups ($X^1$ and $X^2$) are the same or identical. In another embodiment, the photoreactive groups ($X^1$ and $X^2$) are not the same. In one embodiment, the degradable linker ($D^1$ and $D^2$) are the same or identical. In another embodiment, the degradable linker ($D^1$ and $D^2$) are not the same. In one embodiment, the photoreactive groups include one or more first photoreactive groups adapted to attach the linking agent to a surface and one or more second photoreactive groups adapted to initiate photopolymerization.

In one embodiment, the degradable linker is a biodegradable linker that includes an amide bond (also referred to as a peptide bond, or peptide linker). A peptide bond can be cleaved by amide hydrolysis (the addition of water) by enzymatic and non-enzymatic reactions. Proteolysis refers to amide hydrolysis catalyzed by an enzyme. The term "protease" refers to an enzyme that conducts proteolysis. Examples of enzymes capable of hydrolyzing a peptide bond include, but are not limited to, acylase, amidohydrolase, deaminase, trypsin, and alpha-chymotrypsin.

A nonlimiting example of a degradable linker with a peptide bond can be represented by formula I:

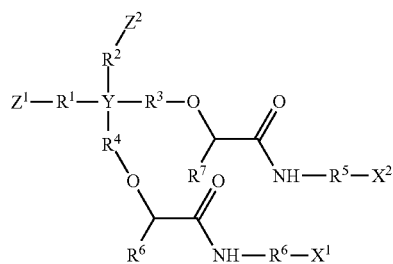

wherein $X^1$ and $X^2$ include, independently, one or more photoreactive groups, including, but not limited to, aryl ketone photoreactive groups, such as acetophenone, benzophenone, anthraquinone, anthrone, anthrone-like heterocycles, their substituted derivatives or a combination thereof; Y represents a core molecule, which can be polymeric or non-polymeric, including for example, non-polymeric molecules such as a hydrocarbon, including linear, branched or cyclic; aromatic or non-aromatic; monocyclic, polycyclic, carbocyclic or heterocyclic; benzene or a derivative thereof; or combinations thereof; $Z^1$ and $Z^2$ represent, independently, one or more charged groups, including positively and negatively charged groups, for example a negatively charged group that includes an organic acid salt, including but not limited to sulfuric acid, sulfonic acid, carboxylic acid, phosphoric acid, phosphonic acid, or a combination thereof; one or more positively charged groups, for example, a quaternary ammonium salt; or a combination thereof $R^1$, $R^2$, $R^3$, and $R^4$ are, independently, spacer elements that can be null, a heteroatom, alkyl or aryl, including, but not limited to cyclic, linear or branched, saturated or unsaturated, aromatic or heteroaromatic, or a combination thereof; $R^5$ and $R^6$ are, independently, spacer elements that can be null, alkyl or aryl, including, but not limited to cyclic, linear or branched, saturated or unsaturated, aromatic or heteroaromatic, or a combination thereof; and $R^7$ and $R^8$ are, independently substituents that can be hydrogen, alkyl or aryl, including, but not limited to cyclic, linear or branched, saturated or unsaturated, aromatic or heteroaromatic, or a combination thereof.

More specific examples of a degradable linker that includes a degradable amide bond include those shown in formulae II and III:

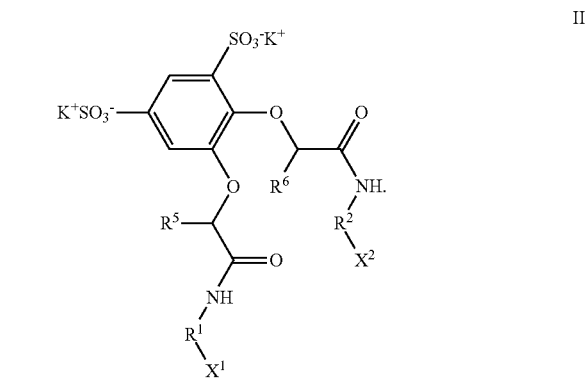

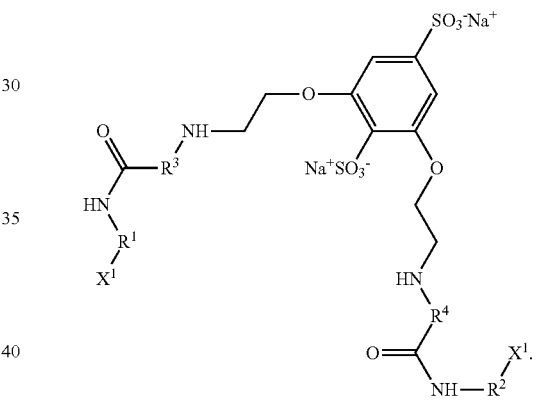

wherein $X^1$ and $X^2$ include, independently, one or more photoreactive groups, including, but not limited to aryl ketone photoreactive groups, such as acetophenone, benzophenone, anthraquinone, anthrone, anthrone-like heterocycles, their substituted derivatives or a combination thereof; and $R^1$, $R^2$, $R^3$, and $R^4$ are, independently, spacer elements, which can be null, alkyl or aryl, including, but not limited to cyclic, linear or branched, saturated or unsaturated, aromatic or heteroaromatic, or a combination thereof and $R^5$ and $R^6$ are, independently substituents that can be hydrogen, alkyl or aryl, including, but not limited to cyclic, linear or branched, saturated or unsaturated, aromatic or heteroaromatic, or a combination thereof.

More specific examples of linkers with degradable peptide bonds are shown in formula IV, below, wherein $R^1$ and $R^2$ are, independently, substituents that can be hydrogen, alkyl or aryl, including, but not limited to cyclic, linear or branched, saturated or unsaturated, aromatic or heteroaromatic, or a combination thereof; and $R^3$ and $R^4$ are, independently, spacer elements, which can be null, alkyl or aryl, including, but not limited to cyclic, linear or branched, saturated or unsaturated, aromatic or heteroaromatic, or a combination thereof

IV

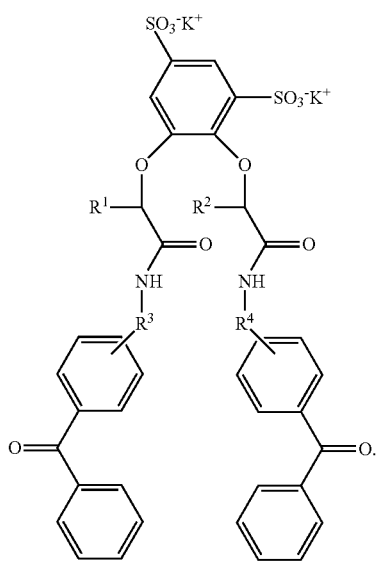

In another embodiment, the degradable linking agent includes one or more ester bonds. Esters can be hydrolyzed to the parent carboxylic acid and an alcohol under acidic or basic conditions. An example of a linker with a degradable ester bond is shown in formula V and VI.

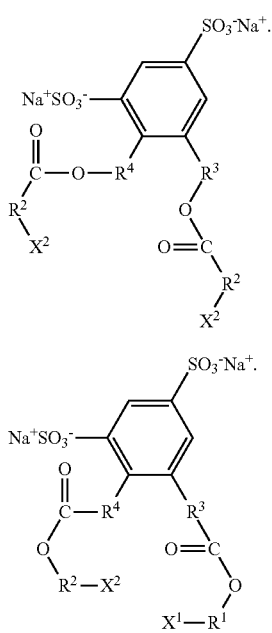

wherein $X^1$ and $X^2$ include, independently, one or more photoreactive groups, including but not limited to aryl ketone photoreactive groups, such as acetophenone, benzophenone, anthraquinone, anthrone, anthrone-like heterocycles, their substituted derivatives or a combination thereof; and $R^1$, $R^2$, are, independently, spacer elements, which can be null, alkyl or aryl, including, but not limited to cyclic, linear or branched, saturated or unsaturated, aromatic or heteroaromatic, or a combination thereof. $R^3$ and $R^4$ are, independently, spacer elements, which can be null, a heteroatom, including, but not limited to O, N or S, alkyl or aryl, including, but not limited to cyclic, linear or branched, saturated or unsaturated, aromatic or heteroaromatic, or a combination thereof.

In another embodiment, the degradable linking agent includes one or more thiocarbamate bonds. Thiocarbamates are carbamates in which the C=O group has been replaced by a C=S group. One example of a degradable linker with a thiocarbamate bond can be represented by formula VII:

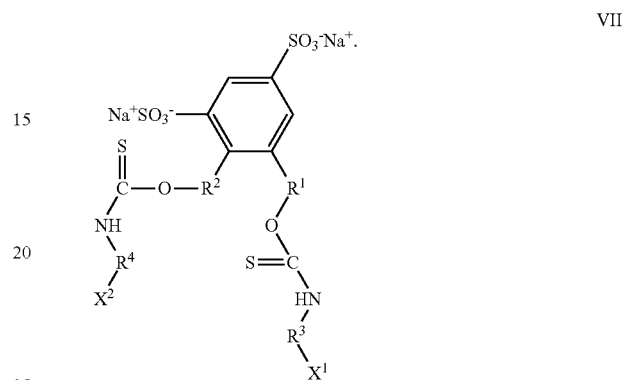

wherein $X^1$ and $X^2$ include, independently, one or more photoreactive groups, including but not limited to aryl ketone photoreactive groups, such as acetophenone, benzophenone, anthraquinone, anthrone, anthrone-like heterocycles, their substituted derivatives or a combination thereof; $R^1$ and $R^2$ are, independently, spacer elements, which can be null, a heteroatom, including, but not limited to O, N or S, alkyl or aryl, including, but not limited to cyclic, linear or branched, saturated or unsaturated, aromatic or heteroaromatic, or a combination thereof; and $R^3$ and $R^4$ are, independently, spacer elements, which can be null, alkyl or aryl, including, but not limited to cyclic, linear or branched, saturated or unsaturated, aromatic or heteroaromatic, or a combination thereof.

Therapeutic Composition

The Lipid Composition

The present therapeutic composition can be a lipid composition that includes a lipid or mixture of lipids. The lipid or mixture of lipids can, for example, be solid (e.g., waxy or paste-like) or semi-solid at room temperature and soft or liquid at the body temperature of a subject.

In an embodiment, the lipid composition includes a lipid with a melting point at or above 40° C. and a lipid with a melting point at or below 20° C. In an embodiment, the lipid composition includes a lipid with a melting point at or above 37° C. and a lipid with a melting point at or below 30° C. In an embodiment, the lipid composition includes a lipid with a melting point of about 35 to about 45° C. and a lipid with a melting point of about 0 to about 35° C.

Lipids that can be employed in the present therapeutic composition include: a marine oil, such as an oil from herring, menhaden, pilchard, sardine, whale, or a mixture thereof; soybean oil, cottonseed oil, corn oil, peanut oil, sunflower oil, safflower oil, olive oil, palm oil, or a mixture thereof; or mixtures thereof. The lipid composition can be a mixture of a lipid that is liquid at room temperature and a lipid that is solid at room temperature. A lipid that is liquid at room temperature is sold under the trade name High Oleic CV-65 canola oil (Cargill Inc., Minnetonka, Minn.). In an embodiment, the oils that are liquid at room temperature are not hydrogenated (e.g., neither partially hydrogenated nor fully hydrogenated). In an embodiment, the lipid that is solid at room temperature is an oil listed above that is partially or fully hydrogenated, for example, fully hydrogenated. A lipid that is liquid at room temperature is sold under the trade name STABLE FLAKE C® and is a cottonseed stearine product (C. & T. Refinery, Inc. of Richmond, Va.)

In certain embodiments, the lipid composition can include: an oil such as vegetable oil, flower oil, animal oil, marine oil (e.g., fish oil), tropical oil (e.g., coconut oil or palm oil), olive oil, peanut oil; lard, butterfat; a saturated fatty acid, for example, butanoic acid, hexanoic acid, octanoic acid, decanoic acid, dodecanoic acid, tetradecanoic acid, hexadecanoic acid, octadecanoic acid, or a mixture thereof; an unsaturated fatty acid, for example, octadecatrienoic acid, eicosanoic acid, eicosenoic acid, eicosatetraenoic acid, eicosapentaenoic acid, docosahexaenoic acid, palmitoleic acid, stearic acid, oleic acid, vaccenic acid, linoleic acid, alpha-linolenic acid, gamma-linolenic acid, behenic acid, erucic acid, lignoceric acid; a natural or synthetic phospholipids, for example, phosphatidylglycerol, phosphatidic acid, phosphatidylcholine, cardiolipin, phosphatidylethanolamine, phosphatidylserine, phosphatidylinositol, dimyristoylphosphatidylcholine, dioleoylphosphatidylcholine, dipalmitoylphosphatidylcholine, distearoylphosphatidylcholine; a mono-, di-, or triacylglycerol; or mixture thereof. Lard is rendered and clarified pork fat and melts around 86° F. (30° C.).

In certain embodiments, the present lipid composition can include one or more of a fat, a wax, a sterol, a phospholipid; a mono-, di-, or tri-glyceride; a fatty acyl, a glycerolipid, a glycerophospholipid, a sphingolipid (e.g., sphingomyelin), a saccharolipid, a polyketide, a sterol lipid, a prenol lipid, or a mixture thereof. Additional suitable lipids include a ceramide, a phosphosphingolipid, a glycosphingolipid, which can include fatty acid moieties that are saturated or mono-unsaturated with chain lengths from 16 to 26 carbon atoms.

The melting point of the present lipid composition can be determined by any one of a variety of art accepted methods. Suitable methods include the Mettler drop point test (see, e.g., ASTM D 3954). Briefly, in this test the sample to be measured is placed in a cup and heated at a given rate. The temperature at which a drop of molten material passes through a standard orifice is recorded. Other methods include the AOCS Method Cc 2-38 (the Wiley melting point), open capillary slip point, and the softening point tests.

Useful methods for making lipid compositions of that are or appear solid at room temperature and components of these compositions include those described in U.S. Pat. No. 6,544,579, which is incorporated herein by reference. The lipid composition can be cooled at ambient temperature or supercooled to provide the lipid coating.

In an embodiment, the lipid composition consists essentially of one or more lipids. In an embodiment, the lipid composition consists of one or more lipids. The lipid is generally not an active agent.

Fatty Acids

The present lipid composition can include one or more fatty acids, meaning free fatty acid not esterified or otherwise derivatized fatty acid. The fatty acid can include or be a salt of the carboxylic acid (e.g., a salt of the fatty acid). Suitable fatty acids include saturated and unsaturated fatty acids. Suitable unsaturated fatty acids include mono-unsaturated fatty acids and polyunsaturated fatty acids. In an embodiment, the fatty acid composition includes a mono-unsaturated fatty acid. In an embodiment, the fatty acid composition includes a saturated fatty acid. In an embodiment, the fatty acid composition includes a saturated fatty acid and a mono-unsaturated fatty acid.

Suitable saturated fatty acids include those including 6 to 28 carbon atoms. In an embodiment, the saturated fatty acid is of the formula $CH_3(CH_2)_nCOOH$, where $4 \leq n \leq 18$. In certain embodiments, n is 4, 5, 6, 7, 8, 9, 10, 11, 12, 13, 14, 15, 16, 17, or 18. In certain embodiments, $6 \leq n \leq 18$, $8 \leq n \leq 16$, or $10 \leq n \leq 14$. In an embodiment, n is 10.

Suitable unsaturated fatty acids include those including 8 to 24 carbon atoms. In an embodiment, the unsaturated fatty acid is of the formula $CH_3(CH_2)_mC=CH(CH_2)_oCOOH$, m and o are independently greater than or equal to 2 and less than or equal to 18. In certain embodiments, m is 2, 3, 4, 5, 6, 7, 8, 9, 10, 11, 12, 13, 14, 15, 16, 17, or 18. In certain embodiments, o is 2, 3, 4, 5, 6, 7, 8, 9, 10, 11, 12, 13, 14, 15, 16, 17, or 18. In certain embodiments, $4 \leq m \leq 18$, $6 \leq m \leq 14$, or $6 \leq m \leq 8$. In certain embodiments, $4 \leq o \leq 18$, $6 \leq o \leq 14$, or $6 \leq o \leq 8$. In an embodiment, m is 7, o is 11 and the double bond is cis. In an embodiment, the unsaturated fatty acid is of the formula $CH_2=CH(CH_2)_pCOOH$ with $3 \leq p \leq 21$.

In an embodiment, the unsaturated fatty acid can be described by C:D where C is the number of carbon atoms and D is the number of double bonds. C can be 6 to 24 and D can be 2 to 6. C and D are integers. In an embodiment, D can be 1 and C can be 6 to 24. The locations and stereochemistry of the double bond can be specified also.

In an embodiment, the fatty acid composition includes a saturated fatty acid with a melting point at or above 30° C. and an unsaturated fatty acid with a melting point at or below 20° C. In an embodiment, the fatty acid composition includes a saturated fatty acid with a melting point at or above 35° C. and an unsaturated fatty acid with a melting point at or below 35° C. In an embodiment, the fatty acid composition includes a saturated fatty acid with a melting point of about 30 to about 45° C. and an unsaturated fatty acid with a melting point of about 0 to about 35° C.

In an embodiment, the lipid coating includes or is made of a plurality of fatty acids. The plurality of fatty acids can be two fatty acids. The lipid coating can be a fatty acid or mixture of (e.g. two) fatty acids. The plurality of fatty acids can be a mixture of fatty acids that are solid at room temperature and soft or liquid at body temperature of the subject. The plurality of fatty acids can be a mixture of fatty acids having a softening temperature greater than room temperature and less than body temperature of the subject. The plurality of fatty acids can be a mixture of fatty acids having a melting point greater than room temperature and less than body temperature of the subject.

Phospholipids

In an embodiment, the lipid composition includes a phospholipid. Suitable phospholipids include, for example, a phosphatidic acid, a phosphatidylcholine, a phosphatidylethanolamine, a phosphatidylserine, or mixture thereof.

Suitable phosphatidylcholines include, for example: 1,2-Didecanoyl-sn-glycero-3-phosphocholine (CAS no. 3436-44-0), 1,2-Dierucoyl-sn-glycero-3-phosphocholine (CAS no. 56649-39-9), 1,2-Dilinoleoyl-sn-glycero-3-phosphocholine (CAS no. 998-06-1), 1,2-Dilauroyl-sn-glycero-3-phosphocholine (CAS no. 18194-25-7), 1,2-Dimyristoyl-sn-glycero-3-phosphocholine (CAS no. 18194-24-6), 1,2-Dioleoyl-sn-glycero-3-phosphocholine (CAS no. 4235-95-4), 1,2-Dipalmitoyl-sn-glycero-3-phosphocholine (CAS no. 63-89-8), phosphatidylcholine purified from egg, phosphatidylcholine purified from soybean, lysophosphatidylcholine, 1-Myristoyl-2-palmitoyl-sn-glycero 3-phosphocholine, 1-Myristoyl-2-stearoyl-sn-glycero-3-phosphocholine, 1-Palmitoyl-2-myristoyl-sn-glycero-3-phosphocholine, 1-Palmitoyl-2-oleoyl-sn-glycero-3-phosphocholine (CAS no. 26853-31-6), 1,2-Distearoyl-sn-glycero-3-phosphocholine (CAS no. 816-94-4), 1-Palmitoyl-2-stearoyl-sn-glycero-3-phosphocholine, 1-Stearoyl-2-myristoyl-sn-glycero-3-phosphocholine, 1-Stearoyl-2-oleoyl-sn-glycero-3-phosphocholine, 1-Stearoyl-2-palmitoyl-sn-glycero-3-phosphocholine, or mixture thereof.

Suitable lysophosphatidylcholines include, for example: 1-Myristoyl-sn-glycero-3-phosphocholine (CAS no. 18194-24-6), 1-Palmitoyl-sn-glycero-3-phosphocholine (CAS no. 17364-16-8), 1-Stearoyl-sn-glycero-3-phosphocholine (CAS no. 19420-57-6), or mixture thereof.

Suitable phosphatidic acids include, for example: 1,2-Dierucoyl-sn-glycero-3-phosphate (Sodium Salt) (CAS no. 80724-31-8), 1,2-Dilauroyl-sn-glycero-3-phosphate (Sodium Salt), 1,2-Dimyristoyl-sn-glycero-3-phosphate (Sodium Salt) (CAS no. 80724-3), 1,2-Dioleoyl-sn-glycero-3-phosphate (Sodium Salt), 1,2-Dipalmitoyl-sn-glycero-3-phosphate (Sodium Salt) (CAS no. 71065-87-7), 1,2-Distearoyl-sn-glycero-3-phosphate (Sodium Salt) (CAS no. 108321-18-2), or mixture thereof.

Suitable phosphatidylethanolamines include, for example: 1,2-Dierucoyl-sn-glycero-3-phosphoethanolamine (CAS no. 988-07-2), 1,2-Dilauroyl-sn-glycero-3-phosphoethanolamine, 1,2-Dimyristoyl-sn-glycero-3-phosphoethanolamine (CAS no. 988-07-2), 1,2-Dioleoyl-sn-glycero-3-phosphoethanolamine, 1,2-Dipalmitoyl-sn-glycero-3-phosphoethanolamine (CAS no. 923-61-5), 1-Palmitoyl-2-oleoyl-sn-glycero-3-phosphoethanolamine, 1,2-Distearoyl-sn-glycero-3-phosphoethanolamine (CAS no. 1069-79-0), or mixture thereof.

Suitable phosphatidylserines include, for example: 1,2-Dilauroyl-sn-glycero-3-phosphoserine (Sodium Salt), 1,2-Dimyristoyl-sn-glycero-3-phosphoserine (Sodium Salt), 1,2-Dipalmitoyl-sn-glycero-3-phosphoserine (Sodium Salt), 1,2-Distearoyl-sn-glycero-3-phosphoserine (Sodium Salt), 1,2-Dioleoyl-sn-glycero-3-phosphoserine (Sodium Salt) (CAS no. 70614-14-1), or mixture thereof.

Bioactive Agent

The term "bioactive agent," refers to an inorganic or organic molecule, which can be synthetic or natural, that causes a biological effect when administered in vivo to an animal, including but not limited to birds and mammals, including humans. A partial list of bioactive agents is provided below. One may choose any one of the bioactive agents to be included alone, or in combination with any other bioactive agent. A comprehensive listing of bioactive agents, in addition to information of the water solubility of the bioactive agents, can be found in *The Merck Index*, Thirteenth Edition, Merck & Co. (2001).

The bioactive agent(s) can be, for example, one or more of the following classes of agents: ACE inhibitors, actin inhibitors, analgesics, anesthetics, anti-hypertensives, anti polymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

In some aspects the bioactive agent includes or is an antiproliferative agent. The antiproliferative agent can be an anti-angiogenesis agent.

In some aspects the bioactive agent includes or is an anti-inflammatory agent.

In some aspects the bioactive agent includes or is a cell response modifier.

In some aspects the bioactive agent includes or is an antithrombotic agent.

In some aspects the bioactive agent includes or is an immunosuppressive agent.

Cell response modifiers include chemotactic factors, such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta).

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The bioactive agent can provide antirestenotic effects, such as antiproliferative, anti-platelet, and/or antithrombotic effects. In some embodiments, the bioactive agent can be selected from anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein Iib/IIIa platelet membrane receptor antibody, coprotein Iib/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The bioactive agent can be an immunosuppressive agent, for example, cyclosporine, CD-34 antibody, everolimus, mycophenolic acid, sirolimus, tacrolimus, and the like.

Additionally, the bioactive agent can be a surface adhesion molecule or cell-cell adhesion molecule. Exemplary cell adhesion molecules or attachment proteins, such as extracellular matrix proteins, include fibronectin, laminin, collagen, elastin, vitronectin, tenascin, fibrinogen, thrombospondin, osteopontin, von Willibrand Factor, bone sialoprotein (and active domains thereof), and hydrophilic polymers such as hyaluronic acid, chitosan and methyl cellulose, and other proteins, carbohydrates, and fatty acids. Other cell-cell adhesion molecules include N-cadherin and P-cadherin and active domains thereof.

An antiproliferative agent, such as sirolimus or paclitaxel, can inhibit neointimal proliferation at a dilated site. An antithrombotic agent, such as heparin, can inhibit clotting.

The present device and method can release an effective amount of the bioactive agent at the desired site. In certain embodiments, the method and device can release about 10% or more of the bioactive agent originally associated with the device, about 20% or more, about 30% or more, about 40% or more, about 50% or more, about 60% or more, about 70% or more, about 80% or more, or about 90% or more. In some aspects the amount of bioactive agent transferred is in the range of about 30% to about 90%.

Transfers of bioactive agent from the present device can be tested in a silicone tube model. Silicone tubing (inner diameter: 0.125 inch; outer diameter: 0.188 inch; wall: 0.0315 inch; Cole-Parmer Instrument Co.) is obtained and cut into 1.5 inch lengths. The silicone tubing pieces are then placed individually in a 4 mL amber glass vial filled with 4 mL of PBS (phosphate buffer saline) pH-7.4, which is preheated in a water bath to 37° C. The present device in its closed configuration is placed in an 8 mL vial (holding 8 mL of phosphate buffer saline at pH 7.4, which is preheated in a water bath to 37° C.) for soaking for 4 min. The device is then slid into the inner lumen of the silicone tube (submerged inside 4 mL vial) and expanded for 30 sec at 4 atm. Pressure is then released and the balloon is removed from the tubing. To determine the amount of bioactive agent (e.g., paclitaxel) transferred to the wall of the inner lumen of the tubing, the tubing is submerged in 4 mL of a mixture of 0.1% glacial acetic acid in methanol for 24 hours. A 350 µL aliquot of the extraction media is then transferred to 96 well plate for drug content measurement by UV (@ 232 nm).

Additional Ingredients

The bioactive agent can be formulated with an excipient. Excipients can improve the stability of the bioactive agent within the therapeutic composition, or can change physical properties of the bioactive agent. Suitable excipients include glycerol, diethylene glycol, sorbitol, sorbitol esters, maltitol, sucrose, fructose, invert sugars, corn syrup, and mixtures thereof. The amount and type of excipient(s) can be based on known standards and techniques. The excipient can be an antioxidant.

Microparticulate

The bioactive agent can be in the form of a microparticulate. The microparticulate can be any three-dimensional particle of size and shape sufficient to be retained in the reservoir and released through the apertures.

The microparticulate can have a spherical, or substantially spherical shape, such as those that are formed from synthetic polymeric materials. In many aspects, the elastic structure of the device is associated with spherical or substantially spherical microparticulate, which is herein referred to as a "microsphere."

However, microparticulate can be used that have noticeably non-spherical shapes or irregular shapes (for example, when examined by microscopy). For example, the microparticulate can have curved surfaces, flat surfaces, or combinations thereof. If desired, the expandable and collapsible structure can be associated with a plurality of microparticulate of a combination of different sizes and/or shapes.

Microparticulate can be in the form of microcrystals or particles that otherwise have crystalline shapes or configurations. Microparticulate with crystalline shapes may be composed of bioactive agent molecules that are arranged in the microparticulate in an orderly repeating pattern extending in all three spatial dimensions. Crystalline shapes can typically be observed under the microscope. Microcrystals may be observed as having rod-like, filament-like, sliver-like, or needle-like shapes.

In the therapeutic composition, microparticulate may also be observed (or exist in) as aggregated or clumped structures. For example, aggregates of microparticulate having rod-like, filament-like, sliver-like, or needle-like shapes can in the therapeutic composition.

In many aspects, microparticulate associated with the device has a greatest average dimension that is less than about 50 µm. For example, for microparticulate can have an elongated shape, with a length along the elongate axis of less than about 50 µm. Size analysis, such as by microscopy, can be used to assess irregular shaped microparticulate or microcrystal. In some cases, the microparticulate has a greatest average dimension in the range of about 20 nm to about 50 µm, about 100 nm to about 50 µm, about 100 nm to about 25 µm, about 100 nm to about 20 µm, or about 100 µm to about 10 µm. In an embodiment, the microparticulate has a greatest average dimension in the range of about 20 nm to about 200 nm, about 30 nm to about 100 nm, or about 50 nm.

Also, in many aspects, the microparticulate have a spherical or substantially spherical shape with an average diameter of about 100 nm or larger. For example, the microparticulate associated with the expandable and collapsible structure can have an average diameter in the range of about 20 nm to about 50 µm, about 100 nm to about 50 µm, about 150 nm to about 25 µm, about 200 nm to about 20 µm, or about 0.3 µm to about 10 µm. In an embodiment, the microparticulate has an average diameter in the range of about 20 nm to about 200 nm, about 30 nm to about 100 nm, or about 50 nm.

In many aspects, microparticulate has an average diameter ("dn", number average) that is less than about 50 µm. Also, in many aspects, the microparticulate can have an average diameter of about 100 nm or larger. For example, the microparticulate can have an average diameter in the range of about 100 nm to about 50 µm, about 150 nm to about 25 µm, about 200 nm to about 20 µm, or about 0.3 µm to about 10 µm. When the microparticulate is in the reservoir, it is generally desirable to utilize microparticulate having an average diameter that is smaller than the thickness of the reservoir.

In some aspects, the microparticulate can also have a low size polydispersity. Low size dispersity means that there is little variation in the size of the microparticulate in the population of microparticulate (as compared to a high size dispersity, which means that there is considerable variation in the size of the microparticulate population).

In some embodiments, the microparticulate can be formed completely or substantially of a selected bioactive agent for treatment or prevention of a condition. In other embodiments, the microparticulate can be formed from a combination of bioactive agents (e.g., two or more different bioactive agents). In other embodiments, the microparticulate can be formed from a bioactive agent and another component that is not intended to provide a therapeutic effect to the subject, such as a polymer that can modulate the release of the bioactive agent from the microparticulate. In other embodiments the microparticulate include two or more components, such as two or more polymers that modulate the release of the bioactive agent from the microparticulate.

Components of the microparticulate can be in mixture with one another in a portion of or all of, the microparticulate. Alternatively, the components can be entirely or substantially separated from one another in the microparticulate. For example, the microparticulate can be formed including a substantially homogenous mixture of a bioactive agent and a release-modulating polymer. As another example, the microparticulate can be formed including a bioactive agent core and a release-modulating polymer shell around the core. The preparation of paclitaxel microparticles has been described in U.S. Pat. No. 6,610,317.

Other techniques for the preparation of microparticulate is known in the art and include precipitation and crystallization. For example, a liquid composition of a bioactive agent in a solvent (e.g., an organic solvent) can be precipitated by addition of an excess of a non-solvent (e.g., water or an aqueous composition). The solvent can be removed from the liquid composition by phase separation, or a comparable technique. The precipitated composition can then be subjected to comminution, which refers to mechanical process that can reduce the size of the precipitated particulates. For example, wet milling can be used to reduce particle size in a liquid composition and produce microparticulate. The precipitated bioactive agent can then be filtered and washed with the non-solvent.

Another process that can be used for the preparation of microparticulate is spray drying. A liquid composition of the bioactive agent and solvent can be atomized and spray deposited on a substrate, and during the process the solvent is evaporated from the droplets. The concentration of the bioactive agent, the droplet size, and the evaporation of the solvent can be determined to provide desired microparticulate formation.

As another example, therapeutic Fab (antibody) fragment microspheres, are described in commonly-assigned copending U.S. provisional patent application No. 60/937,492, filed Jun. 28, 2007 to Slager, et al. Therefore, in another aspect of the invention, the microparticulate is composed of higher molecular weight bioactive agents, such as polypeptides.

Degradable microparticulate can be prepared incorporating various biologically active agents by established techniques, for example, the solvent evaporation technique (see, for example, Wiehert, B. and Rohdewald, P. J. Microencapsul. (1993) 10:195).

In some aspects, the microparticulate includes a bioactive agent and a polymer,
wherein the microparticulate has a structure that includes an inner portion including the bioactive agent and an outer portion including polymer. For example, the microparticulate can have a bioactive agent core and polymer shell.

In some aspects, the core of the microparticulate is formed substantially or entirely of bioactive agent, and the shell includes a biodegradable polymer.

In some aspects, the core of the microparticulate is includes a bioactive agent and a first polymer, and the shell includes a second polymer, such as a biodegradable polymer. For example, the first and second polymers are selected from synthetic biodegradable polymers.

The inner portion (e.g., core) of the microparticulate includes at least most of, if not all, of the bioactive agent present in the microparticulate. Various techniques can be used to prepare microparticulate having inner and outer portions (see, for example, Pekarek, K. J. (1994) Nature 367: 258-60). Some techniques are based on phase separation of a polymer mixture. Many phase separation techniques also involve solvent evaporation.

Microparticulate including an inner portion and an outer portion can be prepared by first preparing a first composition that includes the first polymer and the bioactive agent. The first composition can be treated to provide a homogenous suspension of the first polymer and the bioactive agent. The homogenized first composition can then be combined with a second composition that includes the second polymer. The mixture of the first and second compositions can then be homogenized. After these steps microparticulate can be formed by combining the composition with a solution that promotes formation of the microparticulate, such as a polyvinylalcohol-containing solution. In one mode of practice, the microparticulate can then be recovered by, for example, centrifugation, and then optionally washed, and frozen or lyophilized.

In some specific aspects, the inner portion of the microparticulate include a synthetic biodegradable copolymer, such as poly(lactide-co-glycolide) and an outer portion of the microparticulate include a synthetic biodegradable homopolymer, such as poly(lactide).

The microparticulate can also include one or more non-polymeric compounds to control release of the bioactive agent. For example, the microparticulate can include a soluble metal or metal salt to control release of the bioactive agent. Exemplary metal salts inorganic metal chlorides, fluorides, and oxides. The metal salt can be slightly soluble in water. The microparticulate can be partially or wholly coated with a metal salt.

In some aspects the elastic surface is associated with two or more sets of microparticulate. The use of two or more sets of microparticulate may allow a particular bioactive agent to be released at different rates after the microparticulate have been transferred to tissue, or may allow two different types of bioactive agents to be released to a subject. For example, a first bioactive agent can be released from a first set of microparticulate and a second bioactive agent can be released from a second set of microparticulate.

Two sets of microparticulate can be used if it is desired to deliver two bioactive agents which are mutually incompatible in a particular environment, for example, as hydrophobic and hydrophilic drugs are incompatible in either a polar or non-polar solvent. For example, the first bioactive agent can be a hydrophobic drug present in a first set of microparticulate, and the second bioactive agent can be a hydrophilic drug present in a second set of microparticulate. Useful degradable polymers or degradable copolymers for hydrophobic drugs have a high lactide or high caprolactone content; whereas useful degradable polymers or degradable copolymers for hydrophilic drugs have high glycolide content.

Balloon Catheters

In an embodiment, the insertable medical device can be used for the treatment of diseased vasculature. Suitable bioactive agents that can be released to the vasculature include an antiproliferative agent, an antiinflamatory agent, an antiplatelet agent, or plurality thereof. Suitable antiproliferative agents include paclitaxel. Balloon catheters are commonly used in angioplasty procedures for the treatment of arteries that are diseased. Balloon angioplasty generally involves the dilation or reopening of blocked intraluminal channels.

Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion is then fed over the guidewire until the balloon reaches the target location in the vessel. The balloon is then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

Prior to inflation the balloon can be folded to a compacted configuration for delivery to the target site. A folding process may involve creating "arms" of the balloon material and folding these arms inward (towards the catheter axis) to compact the balloon material. Using such a folding pattern, there will be portions of the balloon material (when the balloon is folded and compacted) that face the outside, and portions of the balloon material that face the inside, the inner-facing portions representing "protected" surfaces. Accordingly, and in another coating embodiment, the inner-facing surfaces of the balloon material include the present coating.

The balloon is typically inflated using a fluid, which is injected through an inflation port. The mechanics of fluid transfer and introduction within balloons vary according to the specific design of the catheter, and are well know in the art.

Exemplary thicknesses for the walls of catheter balloons are in the range of about 5 µm to about 20 µm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon. In some cases, a balloon with a thin wall is used, so as to accommodate the increase in thickness when a coating is formed on the surface.

Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. Balloons fabricated by such processes are suitable as substrates for the coatings according to the present invention. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

The present invention may be better understood with reference to the following examples. These examples are intended to be representative of specific embodiments of the invention, and are not intended as limiting the scope of the invention.

Example

Applying a Scissile Coating to Silicone Tubes with Holes

Holes were poked in thin walled silicone tubing with a piece of 0.014 inch diameter nitinol wire. The tubing was then washed extensively and repeatedly—a sonication, washing with hot water and an alkaline detergent, followed by two more sonications. The tubing was then coated with first coat of a scissile coating. It was immersed in a 2 mg/ml solution of photo-polyvinylpyrrolidone (as described in U.S. Pat. No. 6,007,833) in deionized water, bubbles were removed, and it was subjected to UV cure (Dymax 2000-EC Series UV Floodlamp with a 400 Watt metal halide bulb, approximately 20 cm from light source, illuminated for four minutes). Then the tubing was slowly removed from the solution with a tweezers, drained, fluid was wicked from the interior. The tubing was allowed to dry for about 5 min with a gentle flow of nitrogen through the inside of the tubes.

The tubing was then immersed for a second coat of scissile coating. The second coat was also photo-polyvinylpyrrolidone (as described in U.S. Pat. No. 6,007,833), but in isopropanol. The tubing was then removed from the coating solution, drained, wicked, dried, and uv cured for three minutes.

The tubing was then immersed for a third coat of scissile coating. The third coat was also photo-polyacrylamide (as described in U.S. Pat. No. 6,007,833) in a solvent of 43% deionized water and 57% isopropanol. After 30 seconds in the coating composition, the tubing was removed, drained, quickly wicked, and uv cured for three minutes. The tubing was then dried and uv cured again for 3 minutes.

Preparing and Testing a Double Wall Catheter

Figure 8A:
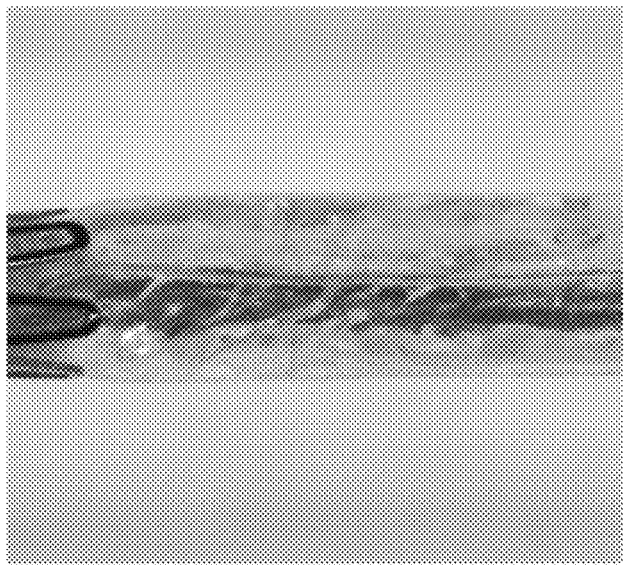
FIGS. 8A through 8C are images of a working model of an embodiment of the present catheter assembly.
Figure 8B:
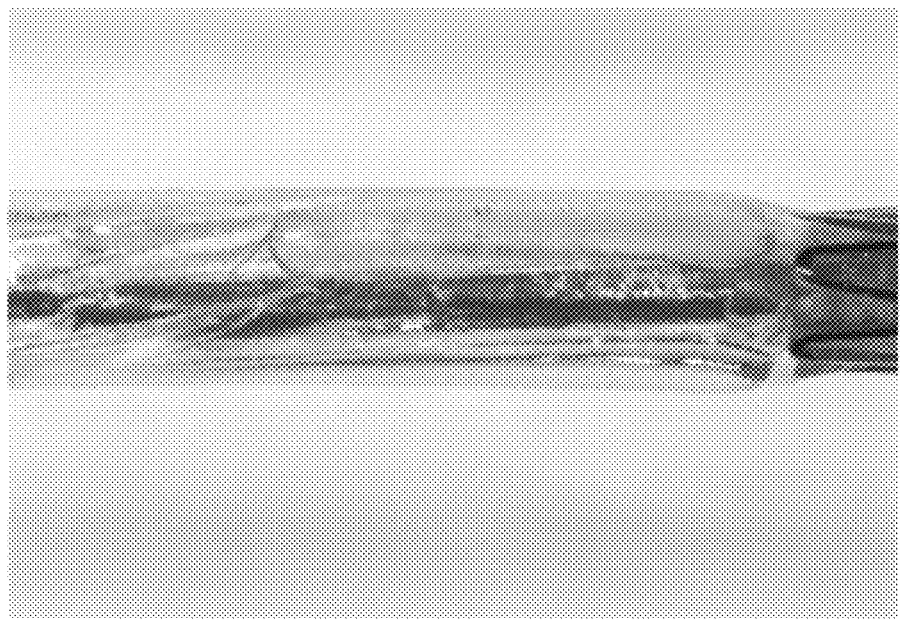
Figure 8C:
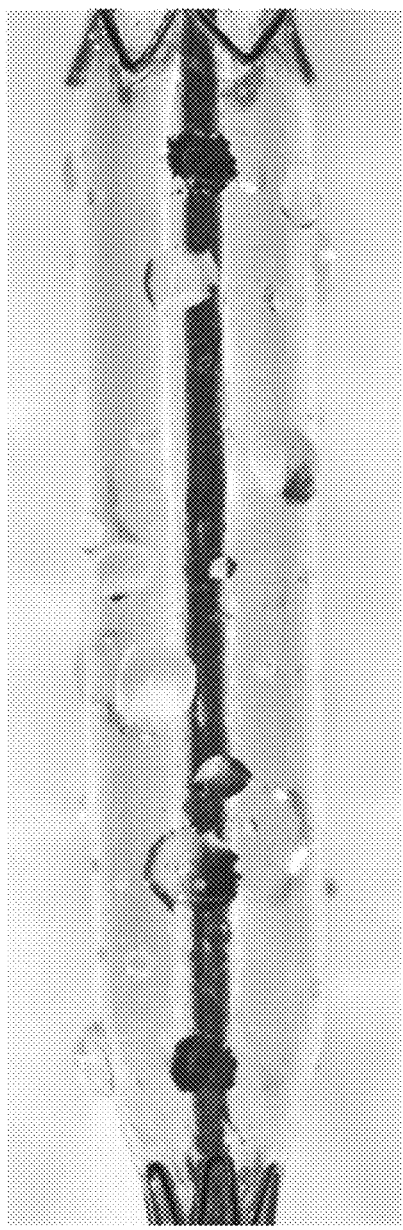

A balloon catheter was obtained from Minnesota Medtec (Maple Grove, Minn.); the balloon was made from nylon with a wall thickness of 5-10 µm. The silicone tubing with the scissile coating was fixed over the first balloon of the catheter. The reservoir was filled by injecting a water miscible therapeutic composition including taxol. The catheter was pressurized at 4 to 8 atm to inflate, and therapeutic composition was expelled from the device (FIGS. 8A, 8B and 8C). FIGS. 8A and 8B are photographs of portions of the double wall catheter before expansion. FIG. 8C shows therapeutic composition expelled from the device after pressurization.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

I claim:

1. A catheter assembly comprising:
   an inner expandable and collapsible structure, an outer expandable and collapsible structure, the inner and outer expandable and collapsible structures each being configured to expand between a contracted state and a dilated state;
   the inner and outer expandable and collapsible structures defining a cavity therebetween, the cavity being configured to contain a benefit composition;
   the outer expandable and collapsible structure defining openings, the openings being configured to be closed when the assembly is in the contracted state and open when the assembly is in the dilated state; when open, the openings provide fluid communication from the cavity to surroundings of the assembly, wherein the outer expandable and collapsible structure comprises an expandable and contractible membrane and an inner photolinkable seal material scissile coating, an outer photolinkable seal material scissile coating, or both inner and outer photolinkable seal material scissile coatings, and in the dilated state, the openings extending through the scissile coating or coatings.

2. The catheter assembly of claim 1, comprising the inner scissile coating.

3. The catheter assembly of claim 1, comprising the outer scissile coating.

4. The catheter assembly of claim 1, wherein the scissile coating or coatings is discontinuous.

5. The catheter assembly of claim 1, wherein the outer expandable and collapsible structure is made of a material that becomes porous when expanded to the dilated state.

6. The catheter assembly of claim 1, wherein the in the openings are closed by cross linking one or more edges that define the opening.

7. The catheter assembly of claim 1, wherein the opening is configured as a circle, a circumferentially oriented slot, an axially oriented slot, a perforation, a flapped opening, a pore, or an ovoid.

8. The catheter assembly of claim 1, further comprising benefit composition disposed in the cavity.

9. The catheter assembly of claim 8, wherein the benefit composition comprises a bioactive agent and a vehicle, the vehicle being in the form of an aqueous solution or a water miscible liquid.

10. The catheter assembly of claim 1 wherein the photolinkable seal material comprises a chemical backbone having attached to it one or more first latent reactive groups and one or more second latent reactive groups.

11. The catheter assembly of claim 10 wherein the photolinkable seal material is compound represented by Formula 1:

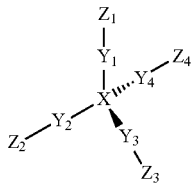

Formula 1 wherein X is the chemical backbone, each of $Y_1, Y_2, Y_3, Y_4$ is an optional spacer, and each of $Z_1, Z_2, Z_3, Z_4$ is the latent reactive group.

12. The catheter assembly of claim 1, wherein the photolinkable seal material comprises water-soluble, degradable linking agent having the formula $Photo^1$-LG-$Photo^2$, wherein $Photo^1$ and $Photo^2$, independently, represent at least one photoreactive group and LG represents a linking group.

13. The catheter assembly of claim 12, wherein the photolinkable seal material is a compound represented by Formula 3:

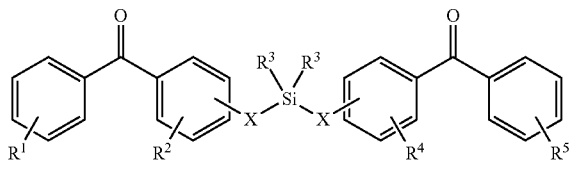

Formula 3 wherein $R^1$ and $R^5$ are independently H, halogen, amine, hydroxyl, alkyl, or a combination thereof; $R^2$ and $R^4$ are independently H, alkyl, or a combination thereof; $R^3$ is alkyl, aryl or a combination thereof; and X is O, N, Se, S, alkyl, or a combination thereof.

14. The catheter assembly of claim 12, wherein the photolinkable seal material is a compound represented by Formula 4:

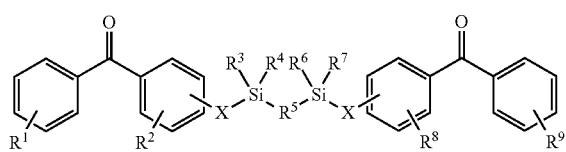

Formula 4 wherein $R^1$, $R^2$, $R^8$, and $R^9$ are independently H, alkyl, halide, hydroxyl, amine, or a combination thereof; $R^3$, $R^4$, $R^6$, and $R^7$ are independently alkyl, aryl, or a combination thereof; $R^5$ is O, alkyl, or a combination thereof; and X is O, N, Se, S, or alkyl, or a combination thereof.

15. The catheter assembly of claim 12, wherein the photolinkable seal material is a compound represented by Formula 5:

Formula 5

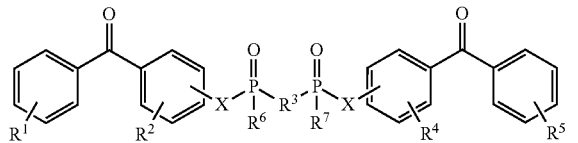

wherein $R^1$, $R^2$, $R^4$, and $R^5$ are independently H, alkyl, halogen, amine, hydroxyl, or a combination thereof; $R^3$ is O, alkyl, or a combination thereof; and X is O, N, Se, S, alkyl, or a combination thereof.

16. The catheter assembly of claim 12, wherein the photolinkable seal material is a compound represented by Formula 2:

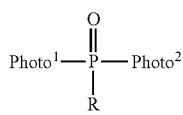

Formula 2 wherein the linking group has a covalent linkage between at least one photoreactive group and the linking group is interrupted by at least one heteroatam and R is alkyl or aryl, a photoreactive group, hydroxyl or salt thereof, or a combination thereof.

17. The catheter assembly of claim 16, wherein R is the hydroxyl salt and includes a counterion that is lithium sodium, potassium, or a combination thereof.

18. The catheter assembly of claim 16, wherein R is cyclic, linear, or branched, saturated or unsaturated, aromatic or heteroaromatic, or a combination thereof.

19. The catheter assembly of claim 16, wherein R is phenyl, methyl, ethyl, isopropyl, t-butyl, or a combination thereof.

20. A catheter assembly comprising:
an inner expandable and collapsible structure, an outer expandable and collapsible structure, the inner and outer expandable and collapsible structures each being configured to expand between a contracted state and a dilated state;
the inner and outer expandable and collapsible structures defining a cavity therebetween, the cavity being configured to contain a benefit composition:
the outer expandable and collapsible structure defining openings, the openings being configured to be closed when the assembly is in the contracted state and open when the assembly is in the dilated state; when open, the openings provide fluid communication from the cavity to surroundings of the assembly, wherein the outer expandable and collapsible structure comprises an expandable and contractible membrane and one or more photolinkable seal material scissile patches or plugs; in the dilated state, an opening extending through a photolinkable seal material scissile patch or plug.

21. A method of delivering a bioactive agent to a site in a body, the method comprising: placing at the site a catheter assembly comprising:
an inner expandable and collapsible structure, an outer expandable and collapsible structure, the inner and outer expandable and collapsible structures being configured to expand between a contracted state and a dilated state;
the inner and outer expandable and collapsible structures defining a cavity therebetween, the cavity containing a benefit composition comprising a bioactive agent;
the outer expandable and collapsible structure comprising openings, the openings being configured to be closed when the assembly is in the contracted state and open when the assembly is in the dilated state;
when open, the openings provide fluid communication from the cavity to surroundings of the assembly; actuating the catheter assembly from the contracted state to the dilated state to release the bioactive agent, wherein the outer expandable and collapsible structure comprises an expandable and contractible membrane and an inner photolinkable seal material scissile coating, an outer photolinkable seal material scissile coating, or both inner and outer photolinkable seal material scissile coatings, and in the dilated state, the openings extending through the scissile coating or coatings.

* * * * *